US012280059B2

(12) United States Patent
Podestá et al.

(10) Patent No.: US 12,280,059 B2
(45) Date of Patent: Apr. 22, 2025

(54) ACYL-CoA SYNTHETASE 4 (ACSL4) INHIBITORY COMPOUND

(71) Applicants: CONSEJO NACIONAL DE INVESTIGACIONES CIENTÍFICAS Y TÉCNICAS (CONICET), Ciudad Autónoma de Buenos Aires (AR); UNIVERSIDAD NACIONAL DE QUILMES, Pcia. de Buenos Aires (AR); UNIVERSIDAD DE BUENOS AIRES, Ciudad Autónoma de Buenos Aires (AR)

(72) Inventors: Ernesto J. Podestá, Ciudad Autónoma de Buenos Aires (AR); Paula M. Maloberti, Ciudad Autónoma de Buenos Aires (AR); Ulises D. Orlando, Pcia. de Buenos Aires (AR); Ana F. Castillo, Pcia. de Buenos Aires (AR); Angela R. Solano, Ciudad Autónoma de Buenos Aires (AR); Pablo Lorenzano Menna, Prov. de Buenos Aires (AR); Daniel E. Gomez, Pcia. de Buenos Aires (AR); Sergio H. Szajnman, Ciudad Autónoma de Buenos Aires (AR); Jessica G. Prada, Pcia. de Buenos Aires (AR); Juan B. Rodriguez, Ciudad Autónoma de Buenos Aires (AR)

(73) Assignees: CONSEJO NACIONAL DE INVESTIGACIONES CIENTÍFICAS Y TÉCNICAS (CONICET), Buenos Aires (AR); UNIVERSIDAD NACIONAL DE QUILMES, Buenos Aires (AR); UNIVERSIDAD DE BUENOS AIRES, Buenos Aires (AR)

(*) Notice: Subject to any disclaimer, the term of this patent is extended or adjusted under 35 U.S.C. 154(b) by 882 days.

(21) Appl. No.: 17/433,174

(22) PCT Filed: Feb. 20, 2020

(86) PCT No.: PCT/IB2020/051433
§ 371 (c)(1),
(2) Date: Aug. 23, 2021

(87) PCT Pub. No.: WO2020/170192
PCT Pub. Date: Aug. 27, 2020

(65) Prior Publication Data
US 2022/0133731 A1    May 5, 2022

Related U.S. Application Data

(60) Provisional application No. 62/808,424, filed on Feb. 21, 2019.

(51) Int. Cl.
*A61K 31/53* (2006.01)
*A61K 31/138* (2006.01)
(Continued)

(52) U.S. Cl.
CPC ............ *A61K 31/53* (2013.01); *A61K 31/138* (2013.01); *A61K 31/337* (2013.01);
(Continued)

(58) Field of Classification Search
CPC .... A61K 31/53; A61K 31/138; A61K 31/337; A61K 31/704; A61K 33/243; A61K 33/24; A61K 45/06; A61P 35/00; C07D 487/04
See application file for complete search history.

(56) References Cited

U.S. PATENT DOCUMENTS

| 9,737,515 B2 | 8/2017 | Podesta |
| 2018/0177763 A1 | 6/2018 | Sanchez-Ramos |

FOREIGN PATENT DOCUMENTS

| WO | WO-2011063223 A1 | 5/2011 |
| WO | WO2018087641 A1 | 5/2018 |

OTHER PUBLICATIONS

Libre Texts, CH 5.6, Diastereomers (Year: 2024).*
(Continued)

*Primary Examiner* — Bruck Kifle
*Assistant Examiner* — Kevin S Martin
(74) *Attorney, Agent, or Firm* — MUNCY, GEISSLER, OLDS & LOWE, P.C.

(57) ABSTRACT

A new compound of formula A for the treatment of aggressive and/or resistant tumors expressing acyl-CoA synthetase 4 (ACSL4) and/or depending on steroids action. More particularly, the compound of the present invention inhibits tumor growth in ACSL4-expressing breast and prostate cancers, inhibits steroid synthesis and sensitizes cells towards chemotherapeutic and hormone therapy agents. Pharmaceutical compositions comprising the ACSL4-inhibitory compound of the invention, pharmaceutical combinations thereof with other anticancer agents and use in therapy.

(Continued)

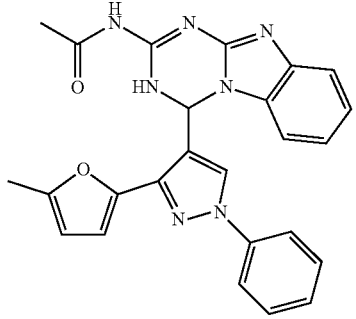

8 Claims, 13 Drawing Sheets

(51) Int. Cl.
A61K 31/337 (2006.01)
A61K 31/704 (2006.01)
A61K 33/243 (2019.01)
A61P 35/00 (2006.01)
C07D 487/04 (2006.01)
A61K 33/24 (2019.01)
A61K 45/06 (2006.01)

(52) U.S. Cl.
CPC .......... *A61K 31/704* (2013.01); *A61K 33/243* (2019.01); *A61P 35/00* (2018.01); *C07D 487/04* (2013.01)

(56) References Cited

OTHER PUBLICATIONS

Marijana Hranjec et al, "Synthesis, crystal structure determination and antiproliferative activity of novel 2-amino-4-aryl-4,10-dihydro[1,3,5]triazino[1,2-]benzimidazoles", Oct. 30, 2011 (Oct. 30, 2011), vol. 1007, p. 242-251, XP028343019; DOI: 10.1016/J.MOLSTRUC.2011.10.054 external link ISSN:0022-2860 [retrieved on Nov. 7, 2011]; (pp. 10).

Boris Brus et al, "Discovery, Biological Evaluation, and Crystal Structure of a Novel Nanomolar Selective Butyrylcholinesterase Inhibitor", Journal of Medicinal Chemistry,vol. 57, No. 19, Sep. 29, 2014 (Sep. 29, 2014), p. 8167-8179, XP055689109, DOI: 10.1021/jm501195e external link, ISSN:0022-2623, (pp. 13).

Boris Brus et al, "Supporting Information Manuscript Title: Discovery, Biological Evaluation, and Crystal Structure of a Novel Nanomolar Selective Butyrylcholinesterase inhibitor Authors", DOI: 10.1021/jm501195e external link, Sep. 16, 2014 (Sep. 16, 2014), Retrieved from the Internet:, URL:http://pubs.acs.org/doi/suppl/10.1021/jm501195e, XP055291053 DOI: 10.1021/jm501195e external link, [retrieved on Jul. 25, 2016], S1 (pp. 27).

Database Registry (online) Chemical Abstracts Service, Columbus, Ohio, US, Apr. 2, 2008 (Apr. 2, 2008), XP055689505, Database accession No. 1011633-31-0 (pp. 1).

* cited by examiner

MDA MB 231 cell line

ACYL-COA SYNTHETASE 4 (ACSL4) INHIBITORY COMPOUND

FIELD OF THE INVENTION

The present invention relates to a compound for the inhibition of the acyl-CoA synthetase 4 (ACSL4) which blocks its action on steroid synthesis and tumorigenesis. More specifically, the present invention relates to a compound that is useful for the treatment of aggressive and/or resistant tumors expressing ACSL4 and/or depending on steroids action. Yet more particularly, the compound of the present invention inhibits tumor growth in ACSL4-expressing breast and prostate cancers, inhibits steroid synthesis and sensitizes cells towards chemotherapeutic and hormone therapy agents. The present invention also refers to pharmaceutical compositions comprising the ACSL4-inhibitory compound of the invention, pharmaceutical combinations thereof with other anticancer agents, its use in therapy and a process for its preparation.

BACKGROUND OF THE INVENTION

Acyl-CoA synthetases (ACS) are a family of enzymes that convert fatty acid to fatty acyl-CoA esters. Currently, five isoforms of the long-chain subfamily of ACS (ACSL; ACSL1, 3-6) have been identified and characterized in rodents and humans [1]. These isoforms differ in their substrate preferences, enzyme kinetics, cellular and organelle location, and regulation. ACSL4 has a marked preference for 20:4 (arachidonic acid, AA) and 20:5 (eicosapentaenoic acid) [1]. The high affinity of ACSL4 for these fatty acids and the low affinity for palmitic acid suggest that the enzyme plays a key role in the metabolism of AA. A second interesting feature of ACSL4 is its tissue distribution. In rats, its mRNA is expressed in various tissues, including the adrenal gland, epididymis, brain, lung, ovary, placenta, and testis. The striking feature of ACSL4 is its abundance in steroidogenic tissues, especially in *Zona fasciculata* and *reticularis* of the rat adrenal gland, Leydig cells of the testis, and luteinized cells of the ovary. It is interesting that although relatively low or null expression levels of ACSL4 have been reported in other adult tissues, this isoform is overexpressed in breast, prostate, colon, and liver cancer specimens.

Unlike the other ACSL isoforms, ACSL4 is encoded on the X chromosome [1]. ACSL4 is also highly expressed in mouse and human cerebellum and hippocampus. The physiological functions of ACSL4 have been studied and include possible roles in polyunsaturated fatty acid metabolism in brain, in steroidogenesis and in eicosanoid metabolism related to apoptosis. ACSL4 expression has also been associated with non-physiological functions such as mental retardation disorder [2-4]. ACSL4 was first associated with cancer due to its abnormal expression in colon and hepatocellular carcinoma. Increased ACSL4 expression, both at mRNA and protein levels, in colon adenocarcinoma cells has been associated with the inhibition of apoptosis and an increase in cell proliferation when compared to adjacent normal tissue [5].

In the last ten years ACSL4 has been proposed as a new target for very aggressive type of cancer, particularly for the triple negative breast cancer (estrogen-receptor-α (ER)-negative, progesterone-receptor (PR)-negative, and human epidermal growth factor 2 receptor (HER2)-non overexpressed) and for the very aggressive prostate cancer. Previous studies have identified ACSL4 gene-expression pattern correlated with triple-negative tumors and prostate cancer [6-10]. Functionally, it was found that ACSL4 is part of the mechanism responsible for increased breast cancer cell proliferation, invasion and migration, both in vitro and in vivo.

The present inventors have shown that mTOR inhibitor rapamycin and rosiglitazone, which is a known ACSL4 inhibitor, can act in combination to inhibit cell growth. In addition, a synergistic effect on cell growth inhibition by the combination of rosiglitazone and tamoxifen, an estrogen receptor α (ERα) inhibitor, was also demonstrated by the present inventors (Orlando et al. 2015, U.S. Pat. No. 9,737,515B2)

According to other strategy, the present inventors have also shown that ACSL4 inhibitors Triacsin C and rosiglitazone can act in combination with chemotherapeutic agents to inhibit cell growth. Furthermore, they have shown a synergistic effect on cell growth inhibition by a combination of such ACSL4 inhibitors with minimal doses of the chemotherapeutic agents doxorubicin and paclitaxel. This synergistic effect was evidenced in triple negative MDA-MB-231 cells (International Publication No. WO 2018/087641).

In addition, the sole expression of ACSL4 displays a distinctive transcriptome and functional proteomic profile, and results show that the most significantly up-regulated gene networks in breast cancer cells overexpressing ACSL4 include genes associated with the regulation of embryonic and tissue development, cellular movement and DNA replication and repair.

ACSL4 expression levels are hormonally regulated through cAMP in steroidogenic cells.

Adrenocorticotropic hormone (ACTH) and luteinizing hormone (LH) [or its surrogate chorionic gonadotropin (CG)] in adrenal gland and testis respectively, regulates ACSL4 expression. The signal transduction pathways include PKA-dependent phosphorylation events in adrenal and Leydig cells, respectively [11]. In the adrenal zona glomerulosa, aldosterone secretion is stimulated by angiotensin II (Ang II) and $K^+$, in addition to ACTH. These stimuli promote phosphorylation events, which are not dependent on cAMP/PKA. Indeed, $K^+$ activates voltage-operated $Ca^{2+}$ channels, while Ang II, bound to Ang II type 1 receptors, acts through the inositol 1,4,5-trisphosphate $IP_3$—$Ca^{2+}$/calmodulin system. In other words, steroid biosynthesis is modulated by hormones, ions, or growth factors through the posttranslational phosphorylation of proteins to increase the synthesis of the steroidogenic acute regulatory protein (StAR) [11].

ACSL4 is a relevant regulator of steroid synthesis throughout the regulation of StAR which controls the rate limiting step in steroid synthesis, i.e., the transport of cholesterol from the outer to the inner mitochondrial membrane [11, 12].

In this context, the present inventors have studied the role of ACSL4 and protein phosphorylation-dephosphorylation in cellular biology and endocrine function of steroidogenic cells.

The transport of cholesterol is regulated by hormones, acting through different signal transduction pathways and is the initial and universal step in the production of steroid hormones.

It is accepted that hormone stimulation of steroid synthesis in adrenal ZF, ZG, and testicular Leydig cells involves the release of arachidonic acid (AA) [11].

Subsequent AA metabolism by lipoxygenase or epoxygenase pathways has been implicated in the regulation of steroid synthesis in adrenal and Leydig cells through the induction of the StAR (steroidogenesis acute regulatory) protein, that works in the transport of cholesterol from the outer to the inner mitochondrial membrane, as indicated above [14]. The present inventors have described a hormonally regulated pathway for the generation and exportation of AA in mitochondria in Leydig and adrenal cells. In this mechanism, free intramitochondrial AA is generated by the action of an acyl-coenzyme A (CoA) synthetase (ACSL4) and a mitochondrial acyl-CoA thioesterase (ACOT2). ACSL4 esterifies free AA to AA-CoA, which could be delivered to ACOT2 and, in turn, releases AA in the mitochondria upon hormone treatment [14].

These two enzymes (ACSL4 and ACOT2) constitute an AA generation/export system, which releases AA in the mitochondrion after the action of the steroidogenic hormones adrenocorticotropin hormone (ACTH) and luteinizing hormone (LH)/chorionic gonadotropin (CG) [14]. When AA is metabolized to lipoxygenated or epoxygenated products, expression of the steroidogenesis acute regulatory (StAR) gene is induced.

Hormone stimulation of AA release, StAR induction, and steroid production involves, as an early and very important step, new synthesis of ACSL4. LH/CG increase ACSL4 protein levels in a time- and concentration-dependent manner.

Here, inventors have surprisingly found a new compound with ACSL4-inhibitory activity, which inhibits tumor growth in breast and prostate cancer, inhibits steroid synthesis and also potentiates the sensitivity of different breast and prostate cancer cell lines to chemotherapy drugs.

SUMMARY OF THE INVENTION

The present invention provides a compound that is a potent and selective inhibitor of ACSL4 cell protein and can be used to inhibit the activity of the ACSL4 enzyme.

More specifically, according to the present invention, this compound can be used to treat diseases mediated by ACSL4 expression and/or mediated by the synthesis of steroid hormones.

Accordingly, this inhibitor is useful for the treatment of any condition mediated by the ACSL4 cell protein/enzyme as well as other steroid-mediated conditions.

Therefore, it is an object of the present invention a new compound (N-(4-(3-(5-methylfuran-2-yl)-1-phenyl-1H-pyrazol-4-yl)-3,4-dihydrobenzo[4,5]imidazo[1,2-a][1,3,5]triazin-2-yl)acetamide) of formula A, an enantiomer, diastereomer, solvate, or pharmaceutical acceptable salt thereof

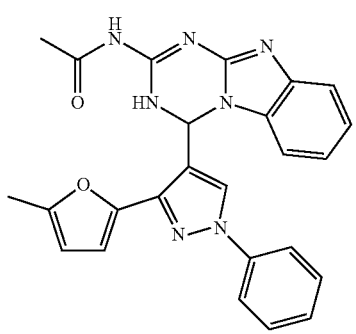

A

According to a preferred object of the present invention, it is provided a process for the preparation of a compound of formula A, which comprises reacting 4-(3-(5-methylfuran-2-yl)-1-phenyl-1H-pyrazol-4-yl)-3,4-dihydrobenzo[4,5]imidazo[1,2-a][1,3,5]triazin-2-amine (formula B) with acetic anhydride.

Preferably, a process for the preparation of a compound of formula A is depicted according to the following Scheme:

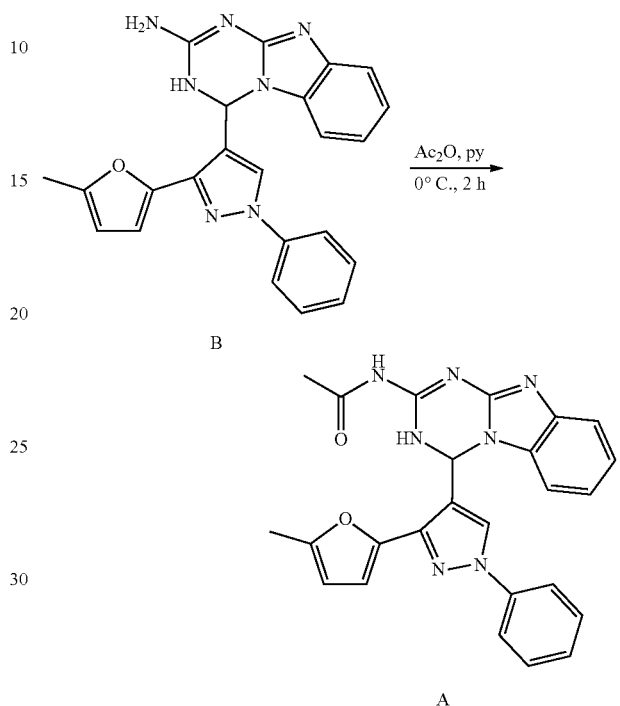

According to another object of the present invention, it is provided a pharmaceutical composition comprising a compound of formula A, together with a pharmaceutically acceptable carrier, excipient or diluent.

According to yet another object of the present invention, it is provided a pharmaceutical combination for inhibiting growth of an ACSL4-expressing tumor comprising a compound of formula A and a chemotherapeutic agent.

According to a preferred embodiment of the present invention, it is provided a pharmaceutical combination for inhibiting growth of an ACSL4-expressing tumor comprising a compound of formula A and a chemotherapeutic agent selected from doxorubicin, paclitaxel and cisplatin.

According to yet another object of the present invention, it is provided a pharmaceutical combination for inhibiting growth of an ACSL4-expressing tumor comprising a compound of formula A and an estrogen receptor (ER) inhibitor.

According to the invention, the ER inhibitor is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen, more preferably the ER inhibitor is 4-OH-tamoxifen.

It is another object of the present invention to provide a method for treating a patient having a tumor expressing ACSL4, the method comprising administering a compound of formula A.

It is another object of the present invention to provide a method for treating a patient having a tumor expressing ACSL4, the method comprising administering a pharmaceutical composition comprising a compound of formula A, together with a pharmaceutically acceptable carrier, excipient or diluent.

It is another object of the present invention to provide a method for treating a patient having a tumor expressing ACSL4, the method comprising administering a compound of formula A in combination with a chemotherapeutic agent. Preferably the chemotherapeutic agent is selected from doxorubicin, paclitaxel and cisplatin.

According to yet another object of the present invention, it is provided a method for treating a patient having a tumor expressing ACSL4, the method comprising administering a compound of formula A in combination with an estrogen receptor (ER) inhibitor.

According to the invention, the ER inhibitor is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen, more preferably the ER inhibitor is 4-OH-tamoxifen.

It is an object of the present invention to provide a compound of formula A, an enantiomer, diastereomer, solvate, or pharmaceutical acceptable salt thereof for use in a method for the treatment of a patient having a tumor expressing ACSL4.

It is another object of the present invention to provide a pharmaceutical composition comprising a compound of formula A together with a pharmaceutically acceptable carrier, excipient or diluent for use in a method for the treatment of a patient having a tumor expressing ACSL4.

It is another object of the present invention to provide a compound of formula A, an enantiomer, diastereomer, solvate, or pharmaceutical acceptable salt thereof in combination with a chemotherapeutic agent for use in a method for treating a patient having a tumor expressing ACSL4. Preferably, the chemotherapeutic agent is selected from doxorubicin, paclitaxel and cisplatin.

It is another object of the present invention to provide a compound of formula A, an enantiomer, diastereomer, solvate, or pharmaceutical acceptable salt thereof in combination with a an estrogen receptor (ER) inhibitor for use in a method for treating a patient having a tumor expressing ACSL4. Preferably, the ER inhibitor is selected from tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

It is another object of the present invention to provide a method for treating a patient having a tumor expressing ACSL4, the method comprising administering a compound of formula B.

It is another object of the present invention to provide a method for treating a patient having a tumor expressing ACSL4, the method comprising administering a pharmaceutical composition comprising a compound of formula B together with a pharmaceutically acceptable carrier, excipient or diluent.

It is another object of the present invention to provide a method for treating a patient having a tumor expressing ACSL4, the method comprising administering a compound of formula B in combination with a chemotherapeutic agent. Preferably the chemotherapeutic agent is selected from doxorubicin, paclitaxel and cisplatin.

According to yet another object of the present invention, it is provided a method for treating a patient having a tumor expressing ACSL4, the method comprising administering a compound of formula B in combination with an estrogen receptor (ER) inhibitor.

According to the invention, the ER inhibitor is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen, more preferably the ER inhibitor is 4-OH-tamoxifen.

It is an object of the present invention to provide a compound of formula B for use in a method for the treatment of a patient having a tumor expressing ACSL4.

It is another object of the present invention to provide a pharmaceutical composition comprising a compound of formula B together with a pharmaceutically acceptable carrier, excipient or diluent for use in a method for the treatment of a patient having a tumor expressing ACSL4.

It is another object of the present invention to provide a compound of formula B in combination with a chemotherapeutic agent for use in a method for treating a patient having a tumor expressing ACSL4. Preferably, the chemotherapeutic agent is selected from doxorubicin, paclitaxel and cisplatin.

It is an object of the present invention to provide a compound of formula B in combination with an estrogen receptor (ER) inhibitor for use in a method for treating a patient having a tumor expressing ACSL4. Preferably, the ER inhibitor is selected from tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

According to another embodiment of the present invention, the method for treating a tumor expressing ACSL4, comprises administering to a subject in need thereof, either simultaneously, sequentially or separately, a compound of formula A and i) one or more chemotherapeutic agents; ii) an estrogen receptor (ER) inhibitor, iii) radiotherapy; iv) conventional surgery; or v) combinations thereof.

According to another embodiment of the present invention, the method for treating a tumor expressing ACSL4, comprises administering to a subject in need thereof, either simultaneously, sequentially or separately, a compound of formula B and i) one or more chemotherapeutic agents; ii) an estrogen receptor (ER) inhibitor, iii) radiotherapy; iv) conventional surgery; or v) combinations thereof.

As used in the present invention, a tumor characterized by the expression of ACSL4 is a tumor selected from the group consisting of prostate cancer, breast cancer and triple negative breast cancer (TNBC).

BRIEF DESCRIPTION OF THE DRAWINGS

The following figures form part of the present specification and are included to further illustrate certain aspects of the present invention, without limiting the scope thereof.

B) Leydig cells were treated with varying concentrations of compound B (inhibitor B), 8Br-AMPc, Triacsin C (for comparative purposes) and 22-R-cholesterol. Data is presented as mean±SD.

Figure 6:
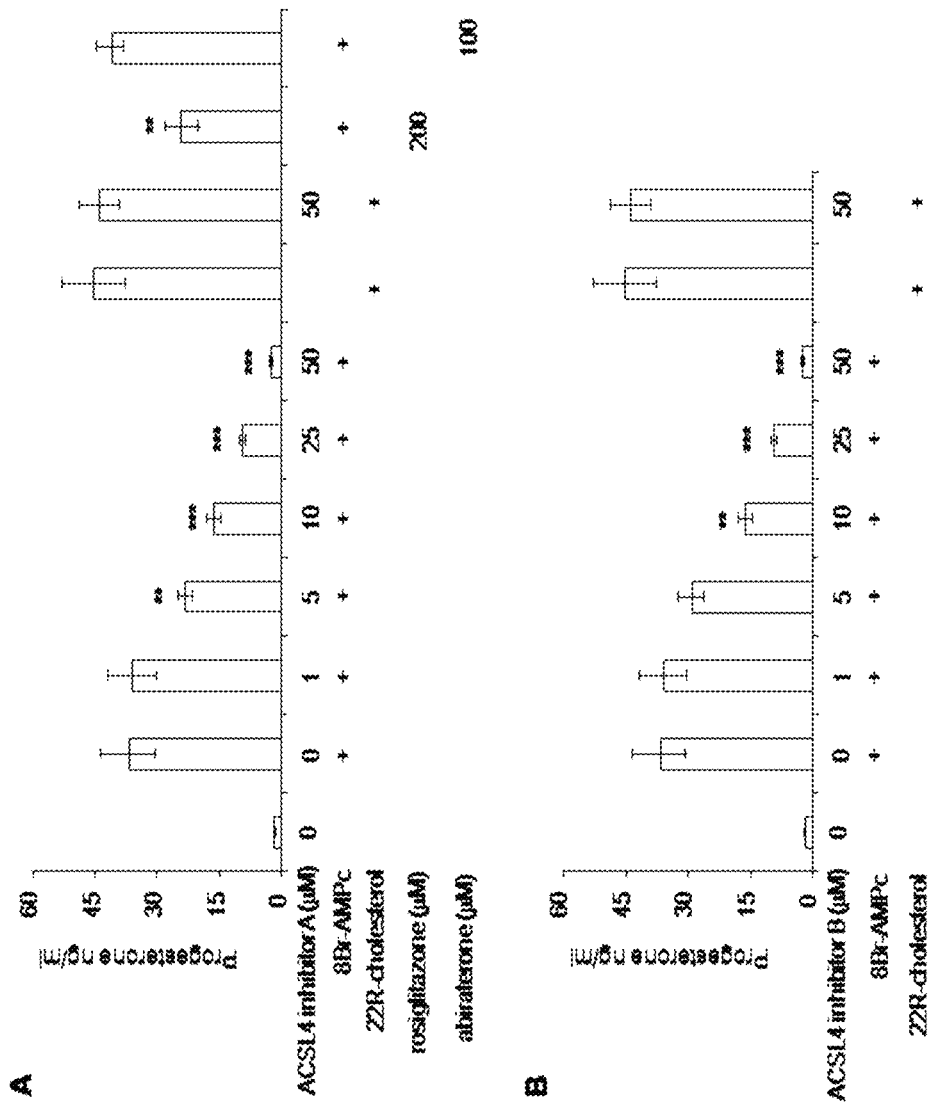

FIG. 6 shows the results obtained by performing a steroidogenesis assay: the effects of ACSL4 inhibition on steroid production (ng/ml) were measured by stimulating Y1 adrenal cells with cAMP and assessing progesterone levels [11]. A) Adrenal cells were treated with varying concentrations of compound A (inhibitor A), 8Br-AMPc (used to stimulate steroid production), 22-R-cholesterol (a permeable cholesterol analog which does not require ACSL4 activation), rosiglitazone (for comparative purposes) and abiraterone (a well-known inhibitor of adrenal steroidogenesis, used as a reference compound). B) Adrenal cells were treated with varying concentrations of compound B (inhibitor B), 8Br-AMPc and 22-R-cholesterol. Data is presented as mean±SD.

Figure 7:
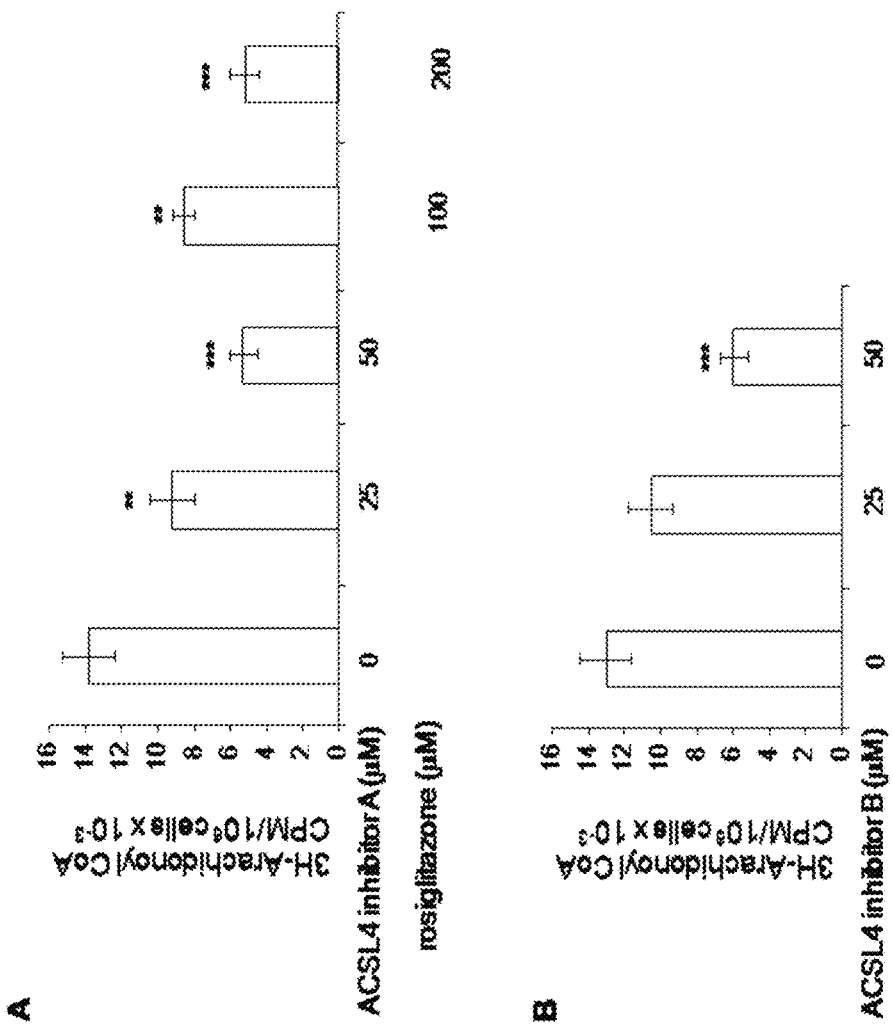

FIG. 7 shows the inhibition of ACSL4 activity in MDA-MB-231 cells through 3H-arachidonic acid (ACSL4 substrate) incorporation. Measured radioactivity incorporation in the cells is expressed as $CPM/10^6$ cells×$10^{-3}$. A) MDA-MB-231 cells were incubated with compound A (inhibitor A) at different concentrations (0, 25, 50 and 200 μM) and rosiglitazone was used as a reference compound (200 μM). B) MDA-MB-231 cells were incubated with compound B at different concentrations (0, 25 and 50 μM). Bars indicate substrate incorporation per dish. Data is presented as mean±SD.

Figure 8:
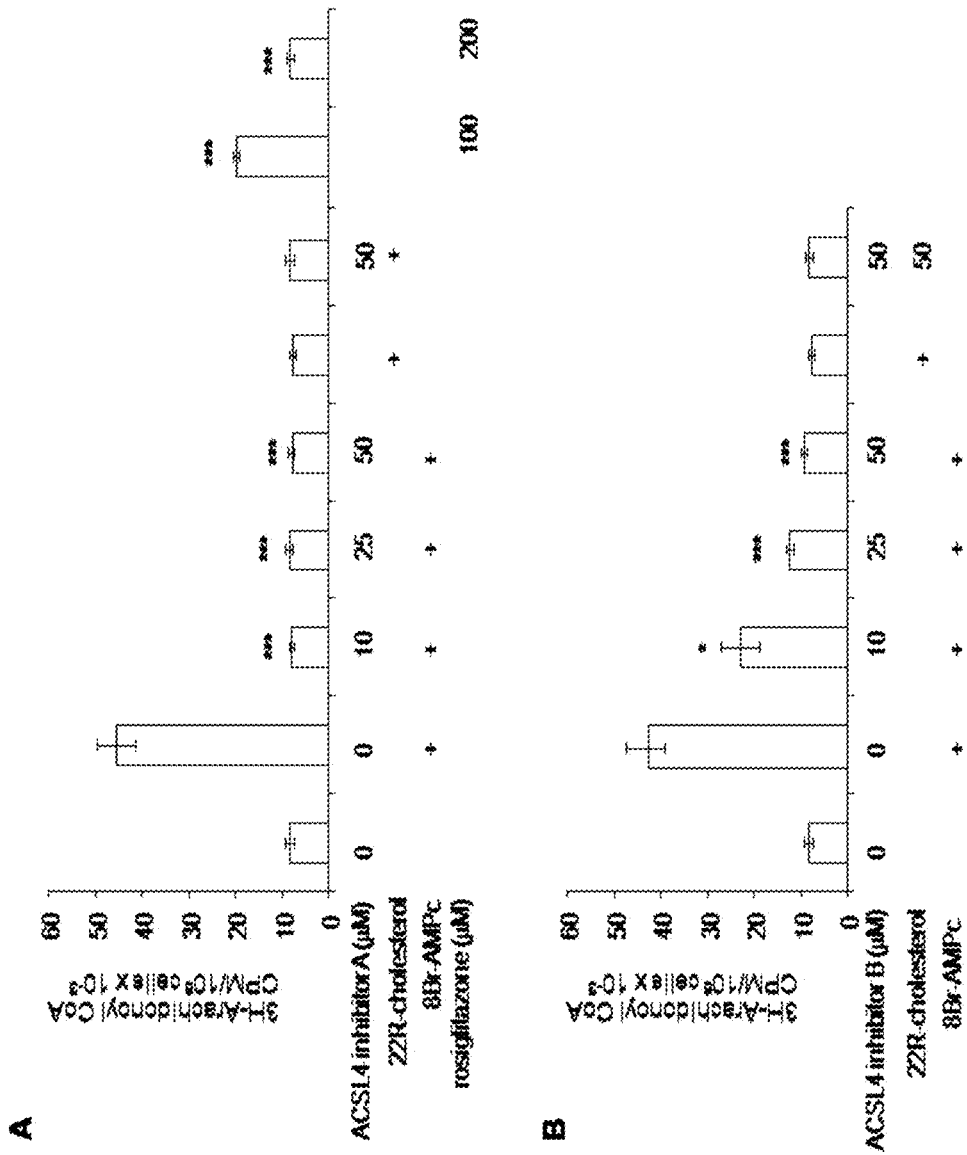

FIG. 8 shows the inhibition of ACSL4 activity in MA-10 Leydig cells through 3H-arachidonic acid (ACSL4 substrate) incorporation. Measured radioactivity incorporation in the cells is expressed as $CPM/10^6$ cells×$10^{-3}$. A) Leydig cells were incubated with compound A (inhibitor A) at different concentrations (0, 10, 25 and 50 μM), 22-R-cholesterol, 8Br-AMPc and rosiglitazone was used as a reference compound (at a concentration of 100 and 200 μM). B) Leydig cells were incubated with inhibitor B at different concentrations (0, 10, 25 and 50 μM), 22-R-cholesterol and 8Br-AMPc. Bars indicate substrate incorporation per dish. Data is presented as mean±SD.

Figure 9:
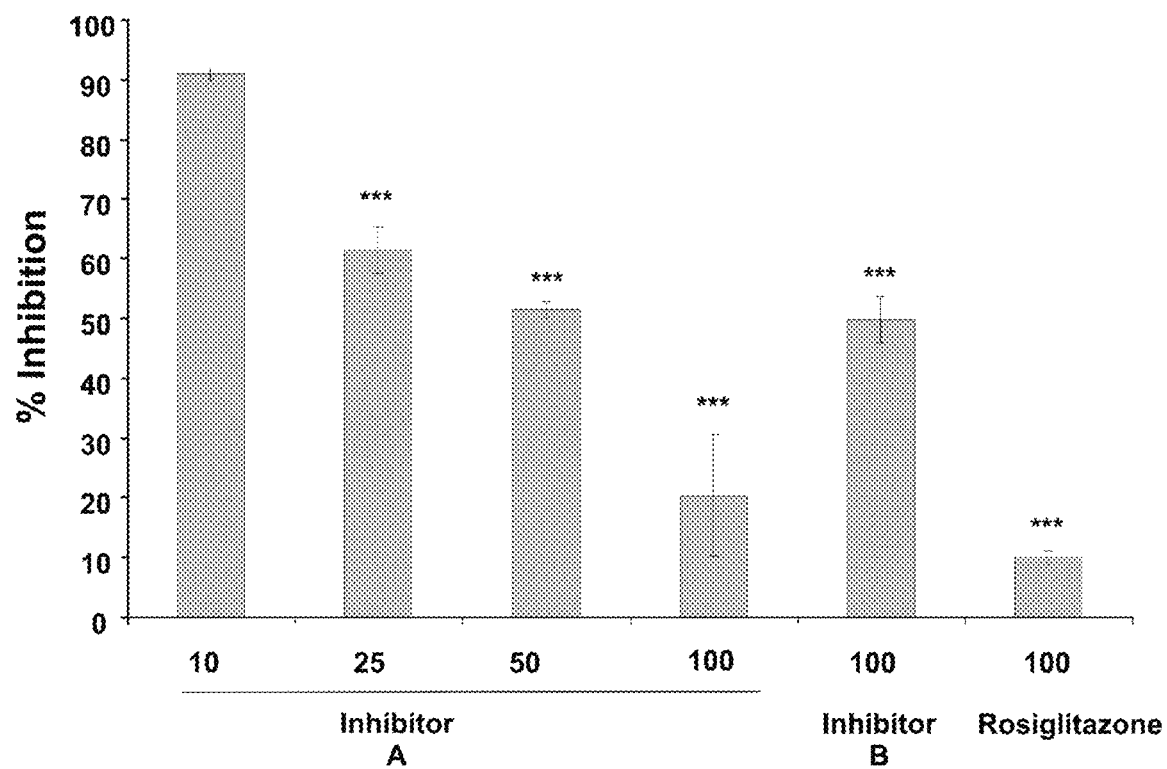

FIG. 9 shows the inhibition of ACSL4 activity using purified ACSL4 protein. Plasmid expressing Flag-tagged human ACSL4 (pCMV6-ACSL4) was transfected into HEK293A cells. 48 h after transfection were sonicated and then flag ACSL4 was immunoprecipitated with anti-Flag antibody (anti-DDK, OTI4C5, Origene). The flag ACL4 was analyzed by Western blot.

Acyl-CoA synthetase activity was measured via a modified protocol by Kim et al. [15], involving the formation of AA-CoA from AA. The radioactivity measured was used to calculate the total enzymatic activity. The results were corrected for blanks (samples without enzyme added). All reactions were confirmed to occur in the linear range. Data is presented as mean±SD.

Figure 10:
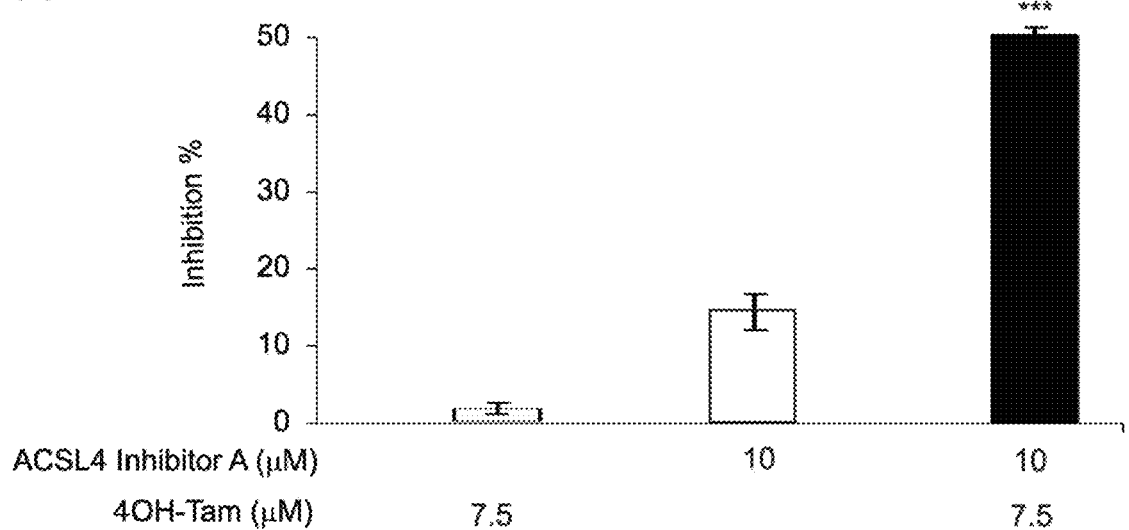
Figure 10:
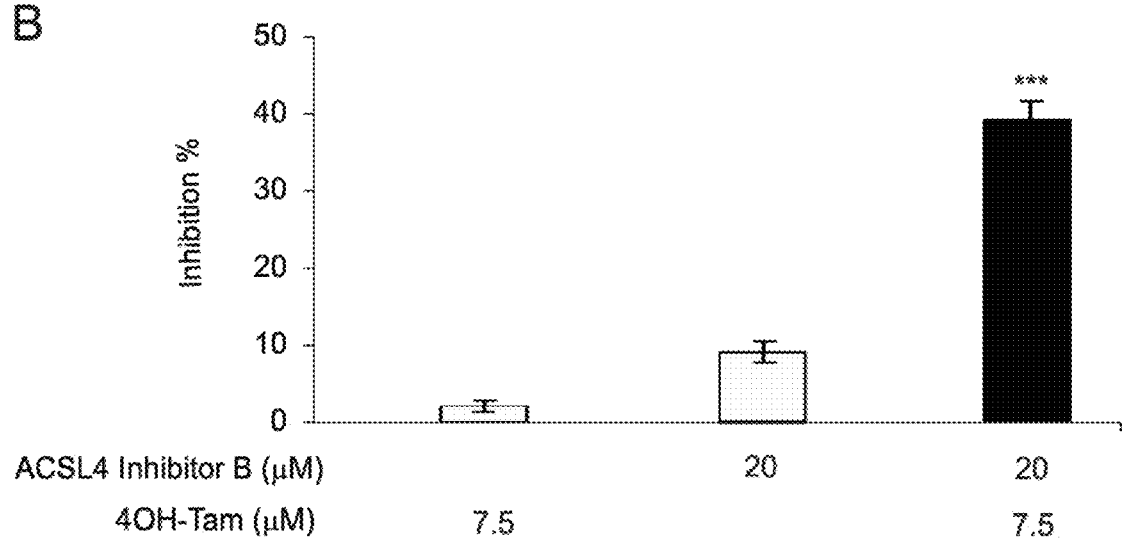

FIG. 10 shows Synergism in MDA-MB-231 cells through combination of the inhibitor of the invention and tamoxifen. MDA-MB-231 cells were plated at a density of 4000 cells/well in 96-well plates with 10% FBS-supplemented D-MEM medium and allowed to adhere overnight at 37° C. in a humidified, 5% CO2 atmosphere. The medium was then changed to serum-free medium. After 24 h, the cells were switched to 10% FBS-supplemented D-MEM medium and incubated with A) compound A (inhibitor A) (10 μM) and/or 4-hydroxytamoxifen (4OH-Tam 7.5 μM) for 72 hours., and B) compound B (inhibitor B) and/or 4-hydroxytamoxifen (40H-Tam 7.5 µM) for 72 hours. Subsequently, cell proliferation was measured by the bromo-deoxyuridine (BrdU) incorporation assay.

Figure 11:
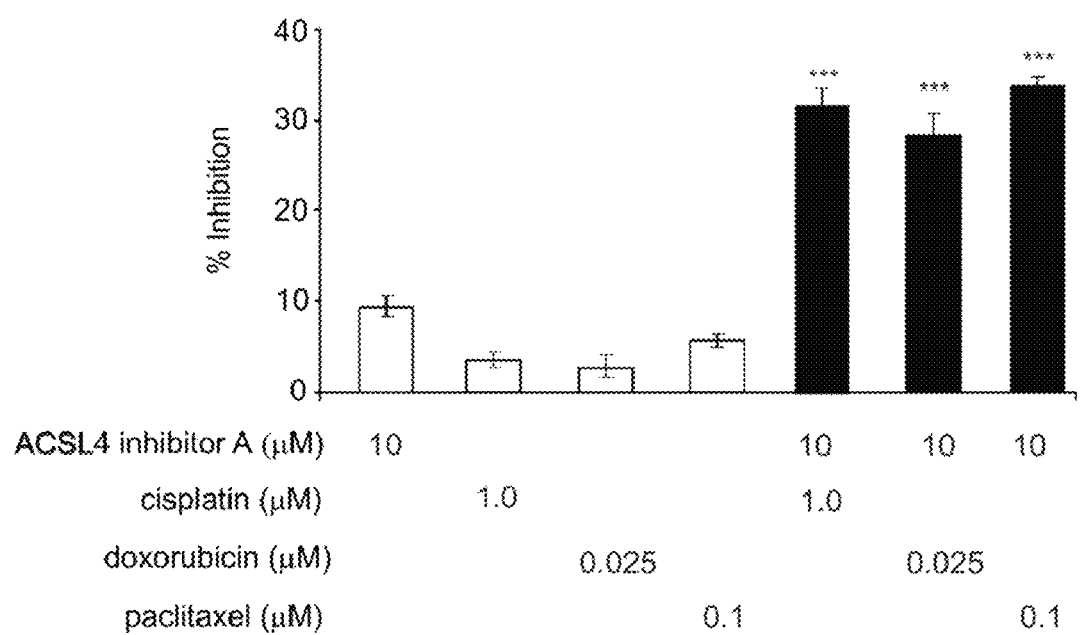

FIG. 11 shows Synergism in MDA-MB-231 cells through combination of the inhibitor of the invention and different chemotherapeutic drugs. MDA-MB-231 cells were plated at a density of 4000 cells/well in 96-well plates with 10% FBS-supplemented D-MEM medium and allowed to adhere overnight at 37° C. in a humidified, 5% CO2 atmosphere. The medium was then changed to serum-free medium. After 24 h, the cells were switched to 10% FBS-supplemented D-MEM medium and then incubated with inhibitor A (10 µM) and/or cisplatin (1 µM), doxorubicin (0.25 µM) and paclitaxel (0.1 µM) for 72 hours. Subsequently, cell proliferation was measured through the BrdU incorporation assay.

Figure 12:
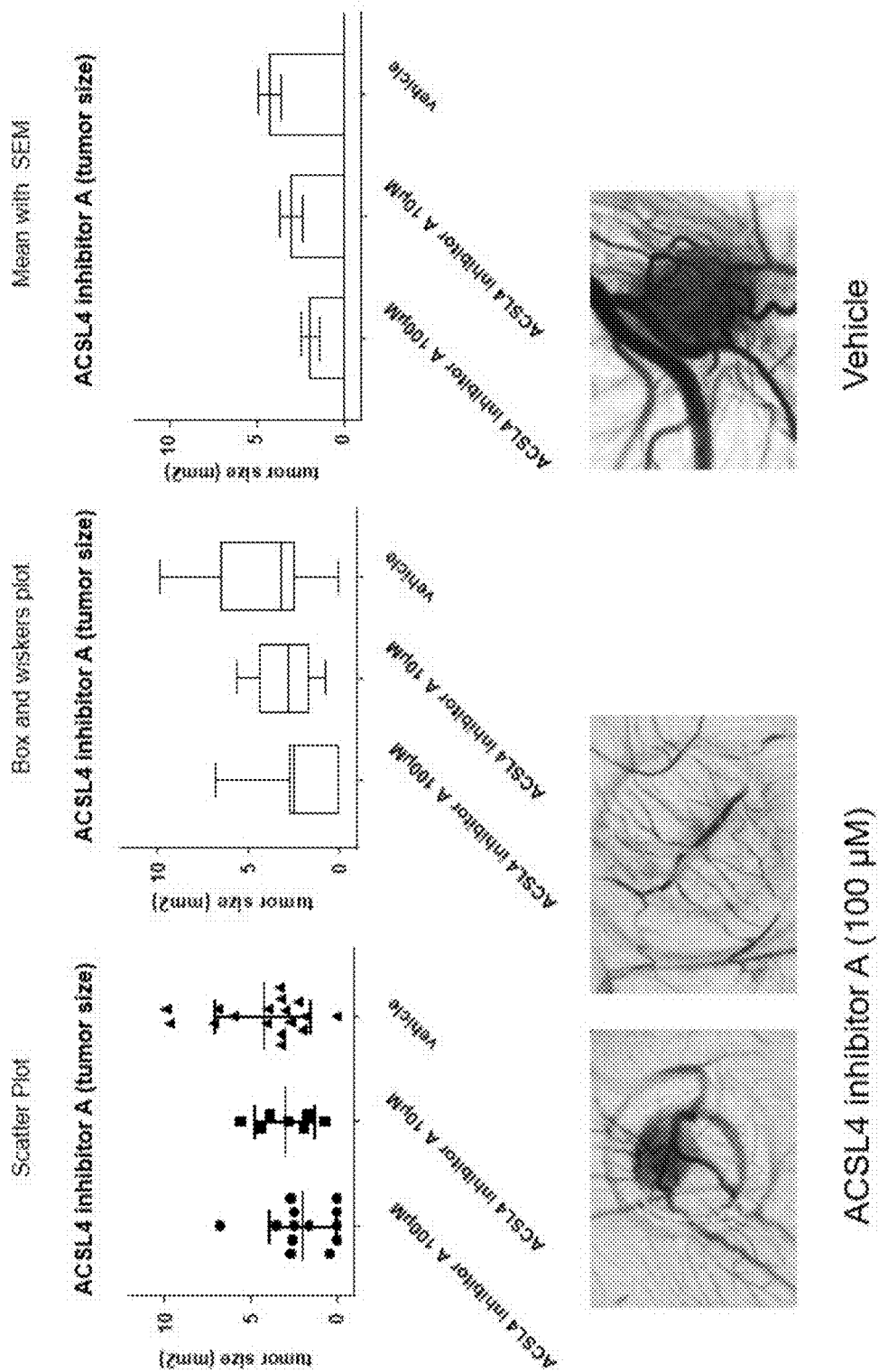

FIG. 12 shows (CAM assay). Breast cancer MDA-MB231 cell line was used as a cell model to assess tumor cell growth. The effects of the compound were compared to those of the vehicle (DMEM). At the endpoint, CAMs were fixed (with paraformaldehyde), excised from the embryo and photographed ex ovo.

Statistical analysis of data was performed by applying the Kruskal-Wallis test which is a nonparametric test that compares three or more unmatched groups and it was used to compare the experimental groups.

Figure 13:
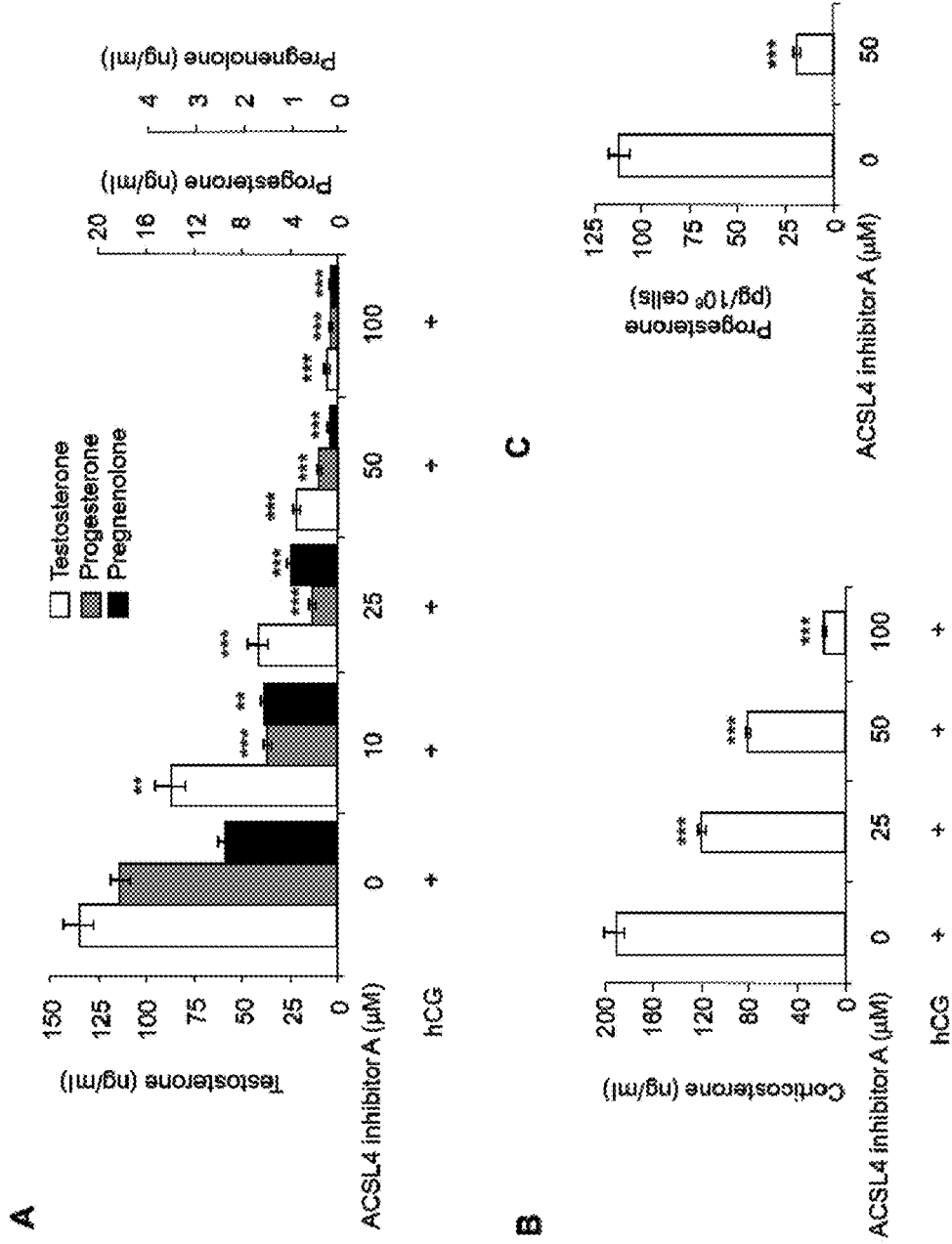

FIG. 13 shows the results obtained by performing a steroidogenesis assay in vivo and steoridogenesis in the Pc-3 cells. Male mice were treated with varying concentrations of inhibitor A and human Chorionic Gonadotrophin (hCG), a well-known activator of testicular steroidogenesis. The effects of ACSL4 inhibition on steroid production (ng/ml) were measured by stimulating the animals with and assessing A) testosterone, pregnenolone and progesterone levels; B) corticosterone and C) steroids in Pc-3 cells. Data is presented as mean±SD.

DETAILED DESCRIPTION OF THE INVENTION

A detailed description is provided below along with accompanying figures. The detailed description is provided in connection with several examples, but is not limited to any particular example. The scope is limited only by the claims, and numerous alternatives, modifications, and equivalents thereof. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

The present inventors demonstrate that the new compound of formula A produces a strong significant effect that reduces tumor growth in a triple negative human breast cancer cell line and also in a very aggressive human prostate cancer cell line.

The present inventors also demonstrate that the combination of inhibition of ACSL4 activity by the compound disclosed herein with a chemotherapy agent or inhibitor of estrogen receptor produces a strong significant effect that reduces growth in a triple negative human breast cancer cell line.

It is remarkable that the dose used of such chemotherapy agent did not produce any effect per se which is an important finding that lead the present inventors to suggest the probability of decreasing side toxic effects of these agents when used in effective doses. The strong significant effect observed by the present inventors is achieved together with a reduction in the doses which also avoids adverse and toxic side effects by the chemotherapeutic agents, also allowing the combination therapy to cover a wide spectrum of signaling pathways which support tumor cells survival.

The present application discloses a new compound having ACSL4-inhibitory activity. The compound described herein blocks ACSL4 action on steroid synthesis and tumorigenesis, and thus, is useful as an antitumor agent.

More particularly, the compound described herein also enhances the cell sensitivity towards chemotherapeutic agents and hormone therapy; therefore, this new inhibitor is specifically suitable for combined pharmacological treatment toward tumor growth inhibition.

The compound with ACSL4-inhibitory activity of the invention inhibits tumor and cell growth in breast and prostate cancer, inhibits steroid synthesis and also potentiates the sensitivity of different breast and prostate cancer cell lines to chemotherapy drugs and hormone treatment. One of the advantages of the compounds of the invention as steroidogenesis inhibitors is that inhibition is effected in the early steps of cholesterol transport into the mitochondria. As a result, steroids do not accumulate—as it happens with other inhibitors—which is beneficial considering the secondary effects of steroid accumulation. Other inhibitors interfere with enzymes that use the P450 cytochrome and also inhibit the hepatic cytochrome that increases the intolerance towards such compounds/inhibitors. On the contrary, the ACSL4-inhibitory compounds of the invention do not inhibit the P450 cytochrome.

According to the present invention it is provided a composition containing an acyl-CoA synthetase 4 (ACSL4) inhibitor selected from the compound A as disclosed herein.

Effective amounts or dosages of the inventive compound A of the application may be ascertained by routine methods, such as modeling, dose escalation, or clinical trials, taking into account routine factors. Actual dosage levels of the active ingredients in the pharmaceutical compositions may be varied. In general, a suitable daily dose of an active compound used in the compositions and methods of the application will be that amount of the compound that is the lowest dose effective to produce a therapeutic effect.

The selected dosage level will depend upon a variety of factors including the activity of the particular compound or combination of compounds employed, or the salts, solvate, and prodrug thereof, the route of administration, the time of administration, the rate of excretion of the particular compound(s) being employed, the duration of the treatment, other drugs, compounds and/or materials used in combination with particular compound(s) employed, age, sex, weight, condition, general health, prior medical history of the patient being treated, and the preference and experience of the physician in charge, and like factors well known in the medical arts.

In another embodiment, the new ACSL4 inhibitor of formula A may be present in an amount of about 0.01 mg to about 600 mg, more suitably in a range of about 5 mg to about 400 mg and more preferably in a range of about 50 mg to 200 mg, per dose unit. All dose units are preferably referred to body weight (i.e. around 70 kg).

More preferably, the new ACSL4 inhibitor of formula A may be present in an amount of about 0.01 mg to about 20 mg, more suitably in a range of about 0.1 mg to about 5 mg and more preferably in a range of about 0.5 mg to about 2 mg, per dose unit. All dose units are preferably referred to body weight, i.e. around 70 kg. Preferably, a typical dosage is in an amount ranging from 2 to 8 mg/70 kg (body weight).

In another embodiment, the ACSL4 inhibitor may be used at a dose of 8-15 mg/kg per day in monotherapy.

According to yet another object of the present invention, it is provided a pharmaceutical combination for inhibiting growth of an ACSL4-expressing tumor comprising a compound of formula A and an estrogen receptor (ER) inhibitor.

According to the invention, the ER inhibitor is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen, more preferably the ER inhibitor is 4-OH-tamoxifen. A typical dosage of 4-OH-tamoxifen may be in an amount ranging from 2 to 50 mg/60 kg per daily dose unit.

According to yet another object of the present invention, it is provided a pharmaceutical combination for inhibiting growth of an ACSL4-expressing tumor comprising a compound of formula A and a chemotherapeutic agent.

According to a preferred embodiment of the present invention, it is provided a pharmaceutical combination for inhibiting growth of an ACSL4-expressing tumor comprising a compound of formula A and a chemotherapeutic agent selected from doxorubicin, paclitaxel and cisplatin.

Chemotherapeutic Agents

Doxorubicin is used herein at a concentration of 0.1 µM in cell culture. Generally, the in vivo dose of doxorubicin in human patients as a monotherapy is approximately 25 mg/m$^2$ via i.v. administration. According to one aspect of the present invention, the doxorubicin dosage used in combination therapy is approximately 2.6 times lower than the minimum dose that produces a significant inhibition when administered alone. In other words, the amount used in combination is 12 times lower than the maximum effective dose when applied alone. This means that the doxorubicin dose used in a combination produces the same inhibitory effect than the drug alone, but at a 12-times lower concentration.

Paclitaxel is used herein at a concentration of 1-5 µM in cell culture. Generally, the in vivo dose of paclitaxel in human patients as a monotherapy is approximately 135 to 175 mg/m$^2$ via i.v. administration every two weeks. According to one aspect of the present invention, the paclitaxel dosage used in combination therapy is half the minimum dose that produces a significant inhibition when administered alone. In other words, the amount used in combination is 5 times lower than the maximum effective dose when applied alone. This means that the paclitaxel dose used in a combination produces the same inhibitory effect than the drug alone, but at a 5-times lower concentration.

Cisplatin is generally used at a dose of 10 to 100 mg/m$^2$ body surface via i.v. administration in a cycle of 3-4 weeks, up to 3 to 6 cycles.

Docetaxel concentration in cell culture for the in vitro assays carried out in the present invention is about 0.01 nM to 0.1 µM. The in vivo dose of docetaxel in human patients is approximately 75 to100 mg/m$^2$ every 21 days, administered as a one-hour infusion. Cmax of docetaxel was determined to be 4.15±1.35 mg/L.

According to the present invention docetaxel is used at a dose of 75 mg/m$^2$ body surface via i. v. administration in a cycle of 3-4 weeks, up to 8 cycles.

Generally, when treating prostate cancer with docetaxel, steroidogenesis inhibitors are co-administered with a synthetic adrenal steroid such as prednisolone. According to another embodiment, an adrenal steroid, such as prednisolone, preferably 50 mg/day of prednisolone, is administered in addition to the present combination therapy for preventing adrenal failure.

The compounds of the present application may be used in pharmaceutical compositions or methods in combination with one or more additional active ingredients in the treatment of the diseases and disorders described herein. As used herein, a "pharmaceutical combination" refers to a product where two or more separate drug preparations are packaged together in a single package or as a unit. Similarly a "pharmaceutical combination" refers to two or more drug preparations packaged separately that according to its proposed labeling is for use only together. In particular, according to the present invention, each drug may be formulated with a suitable carrier/excipient thus forming separate individual preparations, in order to administer them in a simultaneous or sequential way.

Such pharmaceutical combinations may serve to increase efficacy, ameliorate other disease symptoms, decrease one or more side effects, or decrease the required dose of an inventive compound.

The additional active ingredients may be administered in a separate pharmaceutical composition from a compound of the present application or may be included with a compound of the present application in a single pharmaceutical composition. The additional active ingredients may be administered simultaneously with, prior to, or after administration of a compound of the present application. Actual dosage levels of the active ingredients in the pharmaceutical compositions may be varied so as to obtain an amount of the active ingredient that is effective to achieve the desired therapeutic response for a particular subject, such as a patient, composition, and mode of administration, without being toxic to the subject.

As used herein, a "pharmaceutical composition" refers to a product that comprises one or more active ingredients and an optional carrier/excipient. The composition may comprise inert ingredients, as well as any product that results, directly or indirectly, from the combination, complexing or aggregation of any two or more ingredients, or from the dissociation of one or more of the ingredients, or from other types of reactions or interactions of one or more of the ingredients. In general, the pharmaceutical compositions are prepared by uniformly and intimately associating the active ingredient(s) with a liquid carrier/excipient or a finely divided solid carrier/excipient or both, and later, if desired, conforming the product in the desired formulation. In particular, according to the present invention, each active ingredient may be formulated with a suitable carrier/excipient, and after that, if desired, the formulations may be combined to form a single final preparation.

The pharmaceutical compositions of the present invention comprise any composition prepared by mixing active compound(s) and at least one pharmaceutically acceptable carrier/excipient. By "pharmaceutically acceptable", it is meant that the carrier, diluent or excipient must be compatible with the other ingredients of the formulation and must not be harmful for its recipient.

The types of pharmaceutical compositions that can be used according to the present invention include: tablets or pills, chewable tablets, capsules (including microcapsules), powders, powders for reconstitution, solutions, parenteral solutions, aerosol solutions, ointments (creams and gels), suppositories, suspensions, and other types described herein or that are evident for an expert in the field, from general knowledge of the art. The active principle(s), for example, can also be in the form of a complex including cyclodextrins, their ethers or esters.

The compositions and methods of the present application may be utilized to treat a subject, such as a mammal, e.g., human, or a non-human mammal, in need thereof. When administered to an animal, such as a human, the composition or the compound is preferably administered as a pharmaceutical composition comprising, for example, a compound of the application and a pharmaceutically acceptable carrier.

Pharmaceutically acceptable carriers are well known in the art. For example, some examples of materials which can serve as pharmaceutically acceptable carriers include, but are not limited to: sugars, such as lactose, glucose, sucrose or dextrans; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as glycerol or propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; antioxidants, such as ascorbic acid or glutathione; and other non-toxic compatible substances employed in pharmaceutical formulations, such as chelating agents, low molecular weight proteins or other stabilizers or excipients.

The choice of a pharmaceutically acceptable carrier, including a physiologically acceptable agent, depends, for example, on the route of administration of the composition In general, the pharmaceutical compositions of the present invention can be administered by standard routes, such as by parenteral route (for example, intravenous, intravertebral, subcutaneous or intramuscular), oral, tracheal, bronchial, intranasal, pulmonary, buccal, rectal, transdermal or topical. The administration can be systemic, regional or local.

For oral administration, the compounds of the application may be provided in a solid form, such as a tablet, pills, dragees, powers, granules, or capsule, or as a solution, emulsion, or suspension.

To prepare the oral compositions, the active ingredient is mixed with one or more pharmaceutically acceptable carriers, such as sodium citrate or dicalcium phosphate, and/or any of the following: fillers or extenders, such as starches, sucrose, lactose, glucose, mannitol, and/or silicic acid; binders, such as carboxymethylcellulose, gelatin, alginates, polyvinyl pyrrolidone, sucrose and/or acacia; humectants, such as glycerol; disintegrating agents, such as calcium carbonate, agar-agar, potato or tapioca starch, alginic acid, certain silicates, and sodium carbonate; absorption accelerators, such as quaternary ammonium compounds; solution retarding agents, such as paraffin; wetting agents, such as, glycerol monostearate, cetyl alcohol; absorbents, such as kaolin and bentonite clay; lubricants, such as calcium stearate, magnesium stearate, talc, solid polyethylene glycols, sodium lauryl sulfate, and/or mixtures thereof; complexing agents, such as, modified and unmodified cyclodextrins; coloring agents; emulsifying and suspending agents, such as, microcrystalline cellulose, sorbitan esters, ethoxylated isostearyl alcohols, polyoxyethylene sorbitol, bentonite, agar, and tragacanth; and other non-toxic compatible substances employed in pharmaceutical formulations, such as, without limitation, buffering agents, perfuming and preservative agents, sweetening agents, flavoring agents.

Each active ingredient can be separately premixed with the other non-active ingredients, before being mixed to form a formulation or, alternatively, the active ingredients can be mixed together, before being mixed with the inert ingredients to form a formulation.

Soft gelatin capsules can be prepared with capsules that contain a mixture of the active ingredients of the invention, vegetable oil, fat, or other vehicles suitable for soft gelatin capsules. Hard gelatin capsules can contain granules of the active ingredients. Hard gelatin capsules can also contain the active ingredients with solid ingredients in powder, such as lactose, sucrose, sorbitol, mannitol, potato starch, cornstarch, amylopectin, cellulose derivatives or gelatin.

Units for rectal administration can be prepared (i) in the form of suppositories that contain the active substances mixed with a base of neutral fat; (ii) in the form of a rectal gelatin capsule that contains the active substance in mixture with a vegetable oil, paraffin oil or another vehicle suitable for rectal gelatin capsules; (iii) in the form of a ready-to-use microenema; or (iv) in the form of a dry microenema formulation to be reconstituted in a suitable solvent before its administration.

Liquid preparations can be prepared in the form of syrups, elixirs, drops or concentrated suspensions, for example, solutions or suspensions that contain the active principles and the remainder consists of for example, sugar or sugar alcohols, and a mixture of ethanol, water, glycerol, propylene glycol and polyethylene glycol, if desired, such liquid preparations can contain pigment agents, flavoring agent, preservatives, saccharin and carboxymethyl cellulose and other thickening agents. Liquid preparations can also be prepared in dry powder form, reconstituted with suitable solvent before their use. Solutions for parenteral administration can be prepared as the solution of a formulation of the invention in a pharmaceutically acceptable solvent, such as a sterile water solution or non-water solvent, as vegetable oil, esters of long-chain aliphatic acids or propylene glycol. These solutions can also contain stabilizers, preservatives and/or buffers. Solutions for parenteral administration can also be prepared as a dry preparation, reconstituted with a suitable solvent before their use.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intranasal, intraperitoneal, transtracheal, subcutaneous, subcuticular, intraarticular, subcapsular, subarachnoid, intraspinal, and intrasternal injection and infusion.

For parenteral use, the agents of the application may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be reconstituted into a sterile injectable formulation, such as solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

The compositions of the invention to be applied topically on the skin or the scalp can be prepared in the form of ointments (creams or gels). In an embodiment of the invention, an oil emulsion is prepared in water to form a cream. The active compounds in powder form are dissolved in a suitable solvent, such as, for example, propylene glycol. The aqueous phase can alternatively include an alcohol or isopropanol, adding a thickener, for example, Carbomer 934 or 940. The oily phase preferably includes mineral oil, petroleum jelly, cetyl alcohol and/or stearyl alcohol. Emulsifiers which can be used are: polysorbate 80, sorbitan monostearate or others known in the art. Buffering agents, antioxidants and chelating agents may also be added to improve the characteristics of the formulation.

Preparations for topical administration can be prepared for delivery in an aerosol. In these cases, the inhibitory compounds can be admixed with known excipients for aerosol, such as saline solution, alcohol, or fatty acid derivatives, to enhance bioavailability if necessary.

Formulations are also supplied in accordance with the present invention as "kits" that comprise one or more containers that separately contain one or more of the ingredients of the pharmaceutical combination of the invention in a suitable carrier/excipient, for its co-administration. These containers may include indications for the use thereof, such as instructions for use, or a notification in the form prescribed by a governmental agency that governs the manufacture, use or sale of pharmaceutical products, whose notification reflects approval by the agency of the manufacture, use or sale for human use.

The terms "combination therapy" or "co-administration" are intended to embrace the administration of each active agent in a sequential way, in a system that will provide the beneficial effects resulting from the combination of drugs, and it is intended to embrace the co-administration of these agents in a substantially simultaneous way, such as in a single dose unit that has a fixed ratio of these ingredients, or in multiple dose units, separate for each active agent.

The term "treatment" as used herein refers to any treatment of a condition, disease or disorder and includes: (1) inhibiting the disease or condition, that is, deterring its development, (2) alleviating the disease or condition, that is, causing the regression of the condition, or (3) deterring the symptoms of the disease.

According to the present invention, the term "inhibitor of acyl-CoA synthetase 4 (ACSL4)" refers to compounds which are capable of inhibiting the action of acyl-CoA synthetase 4 (ACSL4) on steroid synthesis and tumorigenesis. More specifically, the present invention relates to a compound that is useful for the treatment of aggressive and/or resistant tumors expressing ACSL4 and/or depending on steroids action. Yet more particularly, compound A of the present invention inhibits tumor growth in ACSL4-expressing breast and prostate cancers, inhibits steroid synthesis and sensitizes cells towards chemotherapeutic and hormone therapy agents.

According to yet another object of the present invention it is provided a method for treating a patient having a tumor expressing ACSL4, the method comprising administering to the patient a compound of formula B.

As shown in the Examples below, both inhibitors A and B succeeded in inhibiting the proliferation of highly aggressive breast cancer MDA-MB-231 cells as well as of prostate cancer cells with markedly different results and more potent effects than Rosiglitazone, which is a known ACSL4 inhibitor, that was used as a reference compound.

On the other hand, the present inventors have observed a higher inhibitory effect (lower IC50) of compound A compared to compound B in cell proliferation and ACSL4 activity assays. Moreover and advantageously, the solubility of compound A is higher than the solubility of compound B. Solubility, the phenomenon of dissolution of solute in solvent to give a homogenous system, is one of the important parameters to achieve desired concentration of drug in systemic circulation for desired (anticipated) pharmacological response. The solubility and concentration of compound A in the systemic circulation could be observed in the in vivo experiment in mice since at the dose of 10 µM there was already response in inhibiting steroidogenesis. (see Example 12, FIG. 13 A).

The term "to inhibit" includes its generally accepted meaning that includes "to restrict," "to alleviate," "to improve," and "to slow," "to deter or to invert the progression, severity or a resulting symptom." As used herein, the term "therapy", such as in "drug therapy" or in relation to any medical therapy, includes in vivo or ex vivo diagnostic and therapeutic techniques carried out in a subject in need thereof.

The amount of each active ingredient and the dosage system to treat a disease condition with the compounds and compositions of the invention depends on a variety of factors, including: age, weight, sex and medical condition of the patient, severity of the disease and route and frequency of administration, as well as the particular compound employed, so that it can vary widely.

For all the experimental tests carried out in the present invention, data analysis was performed using GraphPad InStat Software 3.01 (La Jolla, CA, USA). Statistical significance was determined by analysis of variance (ANOVA) followed by Tukey's test.

Items

The present invention may further be described by the following items:

1. A compound (N-(4-(3-(5-methylfuran-2-yl)-1-phenyl-1H-pyrazol-4-yl)-3,4-dihydrobenzo[4,5]imidazo[1,2-a][1,3,5]triazin-2-yl)acetamide) of formula A,

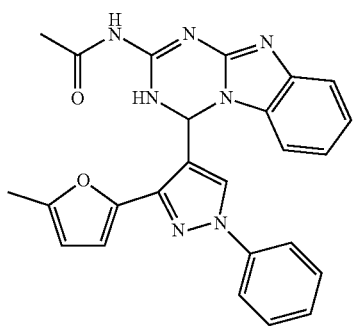

an enantiomer, diastereomer, solvate, or pharmaceutical acceptable salt thereof

2. A process for preparing a compound of formula A, comprising reacting 4-(3-(5-methylfuran-2-yl)-1-phenyl-1H-pyrazol-4-yl)-3,4-dihydrobenzo[4,5]imidazo[1,2-a][1,3,5]triazin-2-amine with acetic anhydride.

3. The process according to item 2, for the preparation of a compound of formula A comprising reacting 4-(3-(5-methylfuran-2-yl)-1-phenyl-1H-pyrazol-4-yl)-3,4-dihydrobenzo[4,5]imidazo[1,2-a][1,3,5]triazin-2-amine (formula B) with acetic anhydride, according to the following reaction:

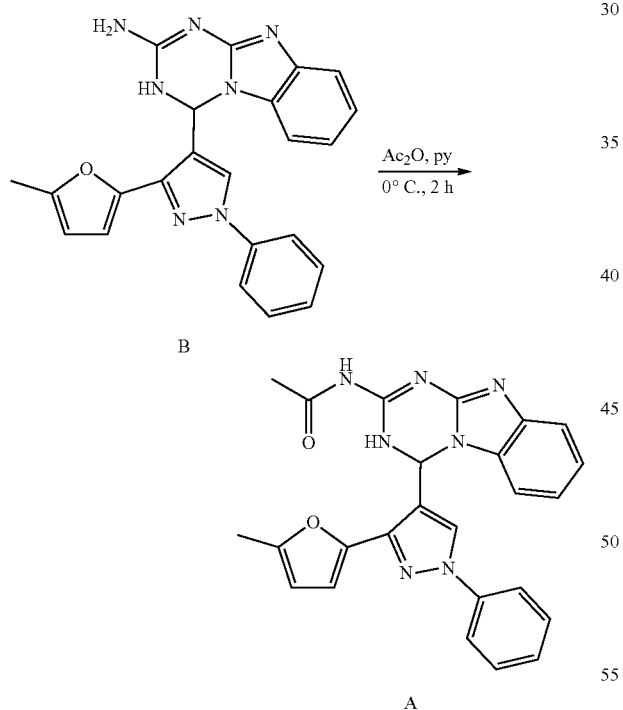

4. A pharmaceutical composition comprising a compound of formula A and a pharmaceutically acceptable carrier, excipient or diluent.

5. A pharmaceutical combination for inhibiting growth of an ACSL4-expressing tumor comprising a compound of formula A and a chemotherapeutic agent.

6. A pharmaceutical combination according to item 5, wherein the chemotherapeutic agent is selected from doxorubicin, paclitaxel and cisplatin.

7. A pharmaceutical combination for inhibiting growth of an ACSL4-expressing tumor comprising a compound of formula A and an estrogen receptor (ER) inhibitor.

8. A pharmaceutical combination according to item 7, wherein the ER inhibitor is selected from tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

9. A method for treating a patient having a tumor expressing ACSL4, the method comprising administering to the patient a compound of formula A.

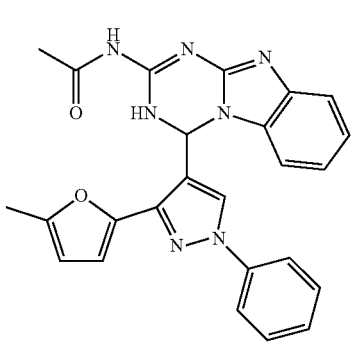

10. A method for treating a patient having a tumor expressing ACSL4, the method comprising administering to the patient a pharmaceutical composition comprising a compound of formula A together with a pharmaceutically acceptable carrier, excipient or diluent.

11. A method for treating a patient having a tumor expressing ACSL4, the method comprising administering a compound of formula A in combination with a chemotherapeutic agent.

12. A method according to item 11, wherein the chemotherapeutic agent is selected from doxorubicin, paclitaxel and cisplatin.

13. A method for treating a patient having a tumor expressing ACSL4, the method comprising administering a compound of formula A in combination with an estrogen receptor (ER) inhibitor.

14. The method according to item 13, wherein the ER inhibitor is selected from tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

15. A method for treating a patient having a tumor expressing ACSL4, the method comprising administering to the patient a compound of formula B

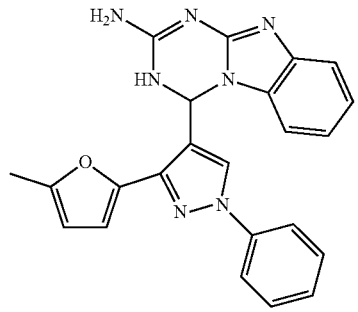

16. The method according to item 15, comprising administering a pharmaceutical composition comprising a compound of formula B together with a pharmaceutically acceptable carrier, excipient or diluent.

17. A method for treating a patient having a tumor expressing ACSL4, the method comprising administering a compound of formula B in combination with a chemotherapeutic agent.

18. The method according to item 17, wherein the chemotherapeutic agent is selected from doxorubicin, paclitaxel and cisplatin.

19. A method for treating a patient having a tumor expressing ACSL4, the method comprising administering a compound of formula B in combination with an estrogen receptor (ER) inhibitor.

20. The method according to item 19, wherein the ER inhibitor is selected from tamoxifen, bazedoxifene, lasofoxifene, ormeloxifene, raloxifene, clomifene, 4-OH-tamoxifen, toremifene, afimoxifene, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

21. A method according to any one of items 9 to 20, wherein the tumor is from prostate cancer, breast cancer and triple negative breast cancer (TNBC).

EXAMPLES

The invention is further illustrated by the following Examples, which are not intended to limit the scope thereof. Instead, the examples set forth below should be understood only as exemplary embodiments for better taking into practice the present invention.

Example 1—Synthesis of (N-(4-(3-(5-methylfuran-2-yl)-1-phenyl-1H-pyrazol-4-yl)-3,4-dihydrobenzo[4,5]imidazo[1,2-a][1,3,5]triazin-2-yl)acetamide) (Compound of Formula A)

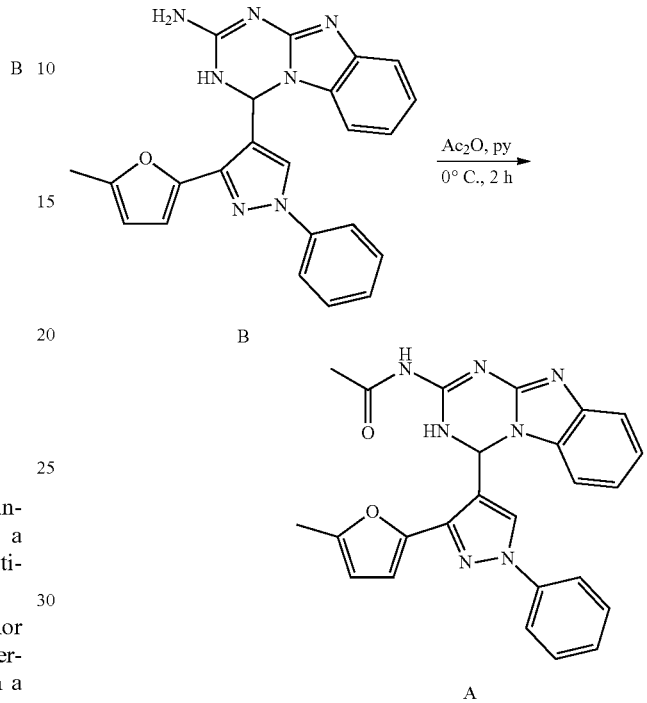

A solution of 4-(3-(5-methylfuran-2-yl)-1-phenyl-1H-pyrazol-4-yl)-3,4-dihydrobenzo [4,5]imidazo[1,2-a][1,3,5]triazin-2-amine (compound of formula B, from Enamine LLC Monmouth Jct., NJ, USA) (5.0 mg, 12.21 μmop in pyridine (0.5 ml), cooled at 0° C. was treated with acetic anhydride (0.5 ml). The reaction mixture was stirred at 0° C. for 3 hours. Then, the solvent was evaporated and the product was purified by column chromatography (silica gel) eluting with a mixture of hexane-EtOAc (19:1) to give 3.0 mg (6.64 μmol, 54% yield) of A as an amorphous solid.

Figure 1:
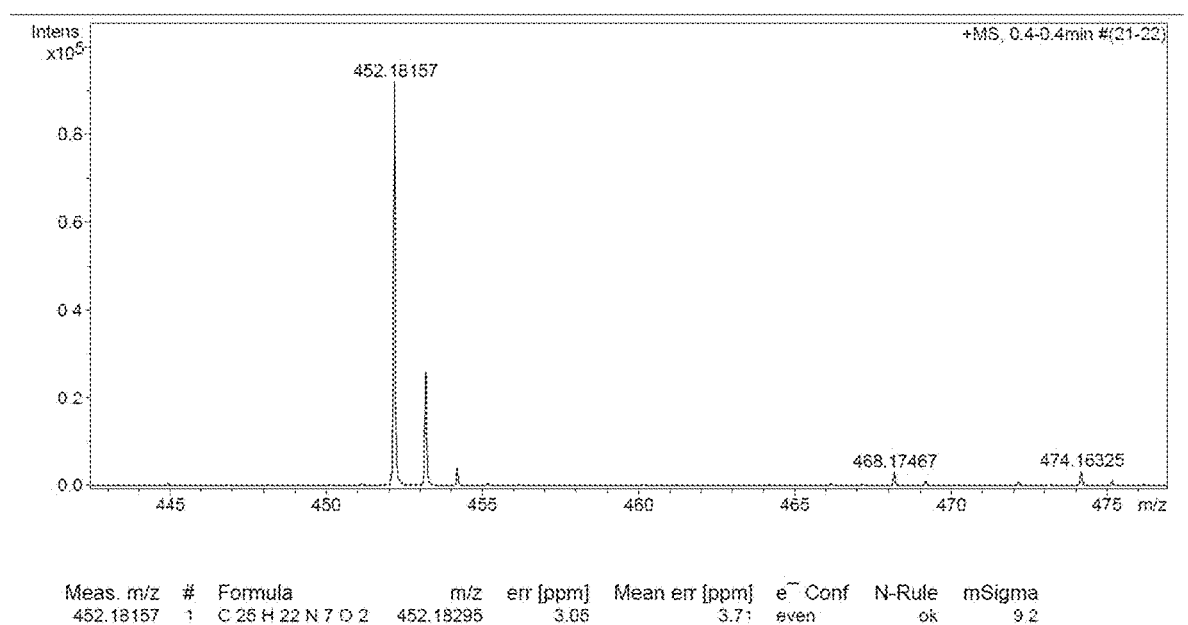
FIG. 1 depicts a mass spectrum obtained by High Resolution Mass spectrometry with Electrospray ionization (HRMS (ESI)) for a sample of compound A as synthetized in Example 1.

HRMS (ESI) calcd. for $C_{25}H_{22}N_7O_2$ $[M+H]^+$ 452,1835; found 452,1816. (FIG. 1)

Example 2

Cell Proliferation Inhibition in a Breast Cancer Cell Line

In this experiment, ACSL4 inhibition was studied through proliferation inhibition of MDA-MB-231 cells. Human breast cancer cell line MDA-MB-231 was generously provided by Dr. Vasilios Papadoupoulus (Research Institute of the McGill University Health Centre, Montreal, Canada) and obtained from the Lombardi Comprehensive Cancer Center (Georgetown University Medical Center, Washington D.C. USA), validated by ATCC Cell Line Authentication Service as 100% matching to ATCC cell line HTB-26 (MDA-MB-231).

MDA-MB-231 cells were plated at a density of 4000 cells/well in 96-well plates with 10% FBS-supplemented D-MEM medium and allowed to adhere overnight at 37° C. in a humidified, 5% CO2 atmosphere. The medium was then changed to serum-free medium.

After 24 h, the cells were switched to 10% FBS-supplemented D-MEM medium and incubated with i) ACSL4 inhibitor A, ii) ACSL4 inhibitor B or iii) rosiglitazone for 96 h. Subsequently, cell proliferation was measured by the bromo-deoxyuridine (BrdU) incorporation assay.

ACSL4 inhibitor A (FIG. 2A) succeeded in inhibiting the proliferation of highly aggressive breast cancer MDA-MB-231 cells at an IC50 of 23 µM. In turn, ACSL4 inhibitor B (FIG. 2B) also succeeded in inhibiting the proliferation of MDA-MB-231 cells, although at higher IC50 (45 µM) and minimal dose than those required for inhibitor A.

Figure 2:
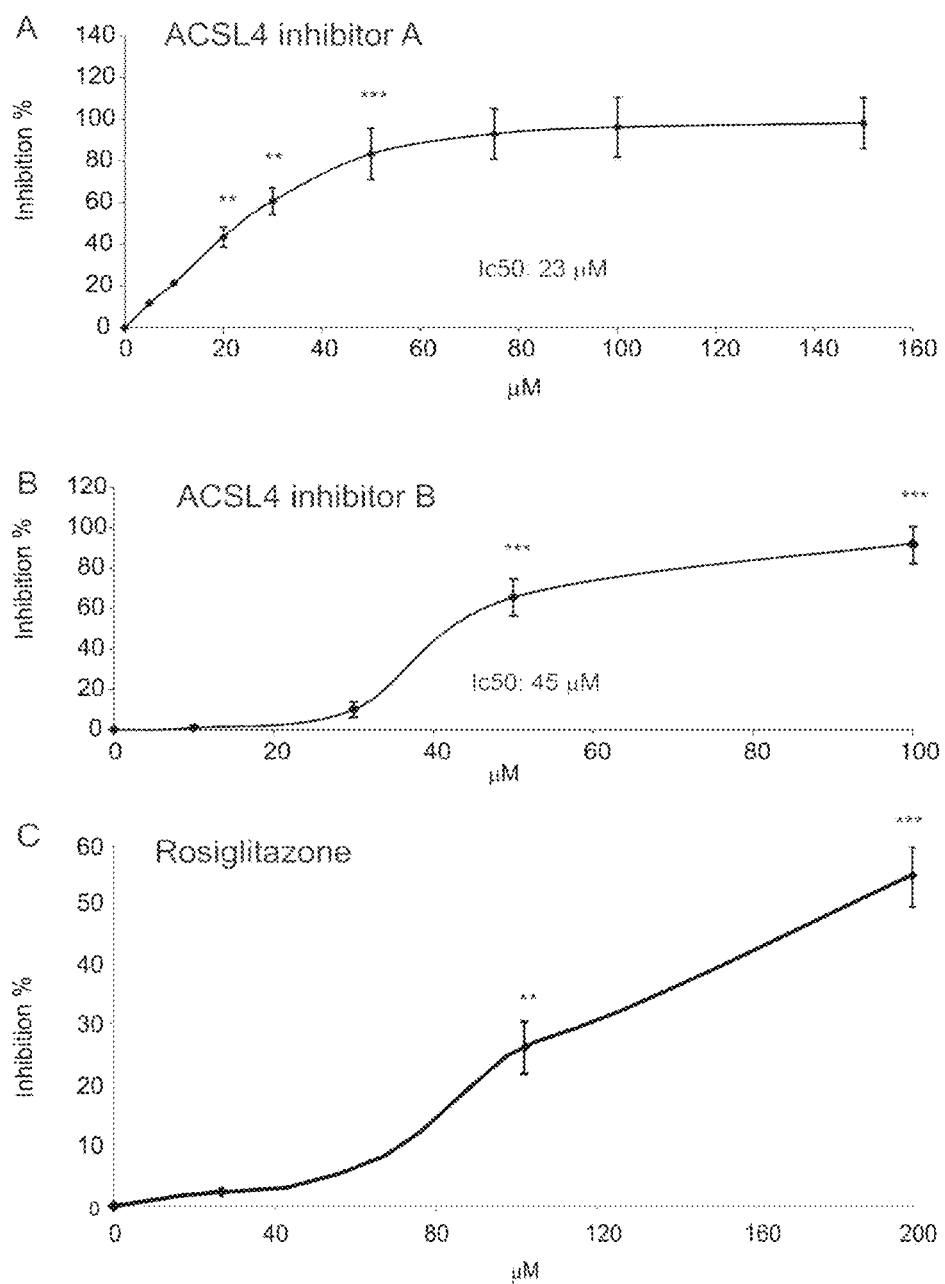
FIG. 2 shows the inhibition of cell proliferation by an ACSL4 inhibitor of the invention measured by the bromodeoxyuridine (BrdU) incorporation assay. MDA MB 231 cells (2000 cells/well) were incubated with varying concentrations of A) a compound of formula A of the invention (inhibitor A) for 72 h. Data is presented as percent inhibition of cell proliferation compared to control cells vs. concentration (μM). Comparative plots are shown for inhibition % by varying concentrations of ACSL4 inhibitors, B) a compound of formula B, and C) Rosiglitazone (as a reference compound) in the same cell line.

Rosiglitazone, which is a known ACSL4 inhibitor, was used as a reference compound, with markedly different results and less potent effects than inhibitors A or B (FIG. 2C).

IC50 (inhibitor A)=23 µM
IC50 (inhibitor B)=45 µM
IC50 (Rosiglitazone)=180 µM

Example 3

Cell Proliferation Inhibition in a Prostate Cancer Cell Line

ACSL4 inhibition was also assessed through proliferation inhibition in the Pc-3 cell line. PC-3 human prostate cancer cell line was generously provided by Dr. Susana Nowicky and validated by ATCC Cell Line Authentication Service as 100% matching to ATCC cell line CRL-1435 (PC-3).

PC-3 cells were plated at a density of 4000 cells/well in 96-well plates with 10% FBS-supplemented D-MEM medium and allowed to adhere overnight at 37° C. in a humidified, 5% CO2 atmosphere. The medium was then changed to serum-free medium. After 24 h, the cells were switched to 10% FBS-supplemented D-MEM medium and incubated with i) ACSL4 inhibitor A, ii) ACSL4 inhibitor B or iii) rosiglitazone for 96 h. Subsequently, cell proliferation was measured by the bromo-deoxyuridine (BrdU) incorporation assay.

ACSL4 inhibitor A (FIG. 3A) succeeded in inhibiting the proliferation of prostate cancer cells at an IC50 of 27 µM. In turn, ACSL4 inhibitor B (FIG. 3B) also succeeded in inhibiting the proliferation of Pc-3 cells, although at higher IC50 (48 µM) and minimal dose than those required for inhibitor A.

Figure 3:
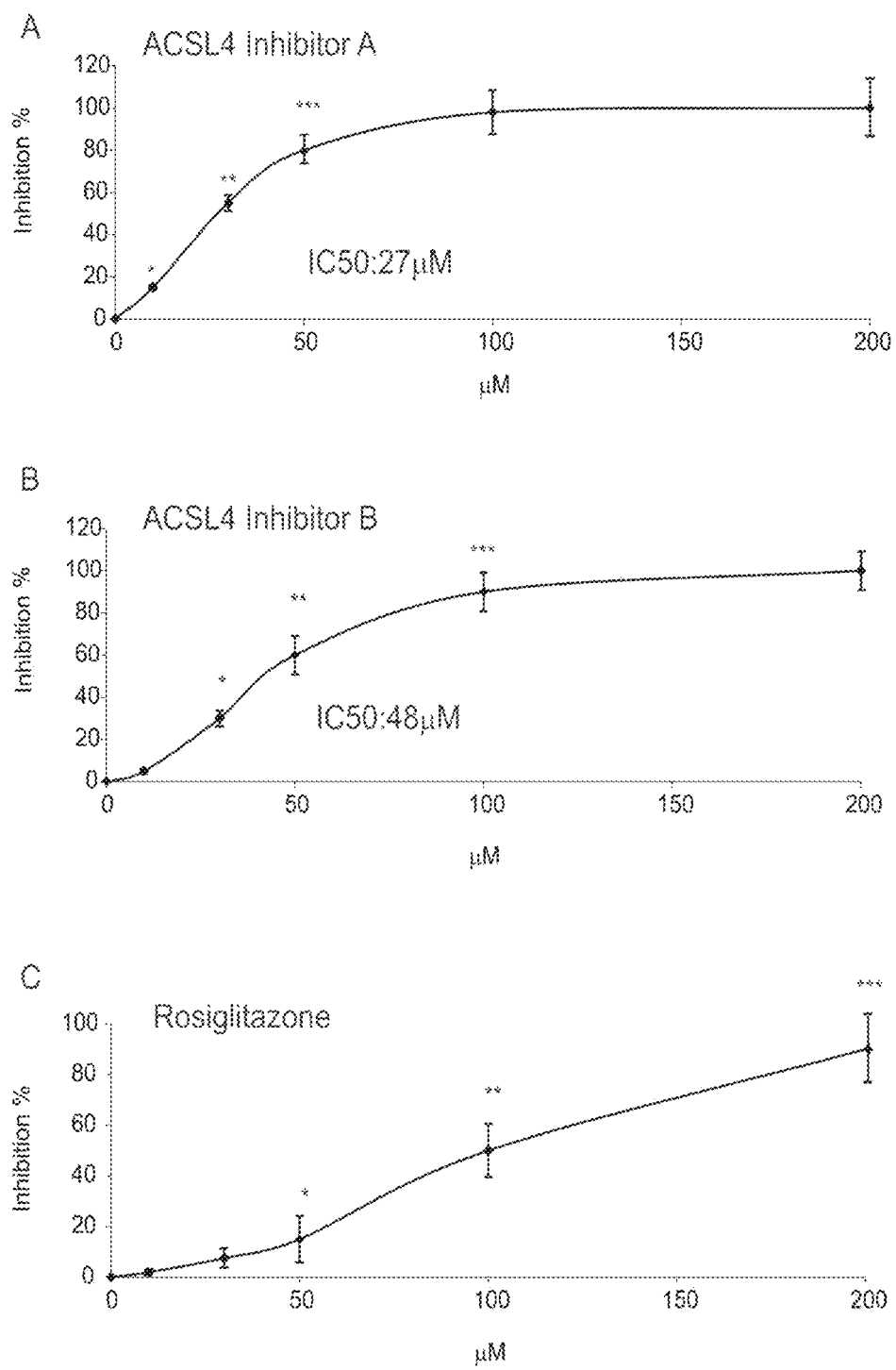
FIG. 3 shows the inhibition of cell proliferation by an ACSL4 inhibitor of the invention measured by the bromodeoxyuridine (BrdU) incorporation assay. Prostate cancer cells of the Pc-3 cell line were incubated (2000 cells/well) with varying concentrations of A) a compound of formula A of the invention (inhibitor A) for 72 h. Data is presented as percent inhibition of cell proliferation compared to control cells vs. concentration (μM). Comparative plots are shown for inhibition % by varying concentrations of ACSL4 inhibitors, B) a compound of formula B, and C) Rosiglitazone (as a reference compound) in the same cell line.

Rosiglitazone was used as an ACSL4 inhibitor reference compound, with markedly different results and less potent effects than inhibitors A or B (as shown in FIG. 3C).

IC50 (inhibitor A)=27 µM
IC50 (inhibitor B)=48 µM
IC50 (Rosiglitazone)=100 µM

Example 4

Migration Assay in MDA-MB-231 and Pc-3 Cells

Cellular migration was measured by the wound healing assay. Cells ($7 \times 10^5$ cells per well) were seeded in six-well plates. Cells were kept in complete (10% FBS) medium. Cell monolayer was wounded with a plastic tip across the monolayer cells. Wound closures were photographed by a phase contrast microscopy (40×) in the time point 4, 8 and 12 h after scraping. The width of the wound was determined with the Image Pro-Plus program.

For the wound healing assay, cells were incubated with either vehicle (control), the compound of the invention (inhibitor A) (50 µM) and Rosiglitazone (200 µM). At the specified time points, the distance between the wound edges was measured using Image-Pro Plus software. Results are shown in FIG. 4A-D. Data represent the mean±SD of three independent experiments.

Figure 4:
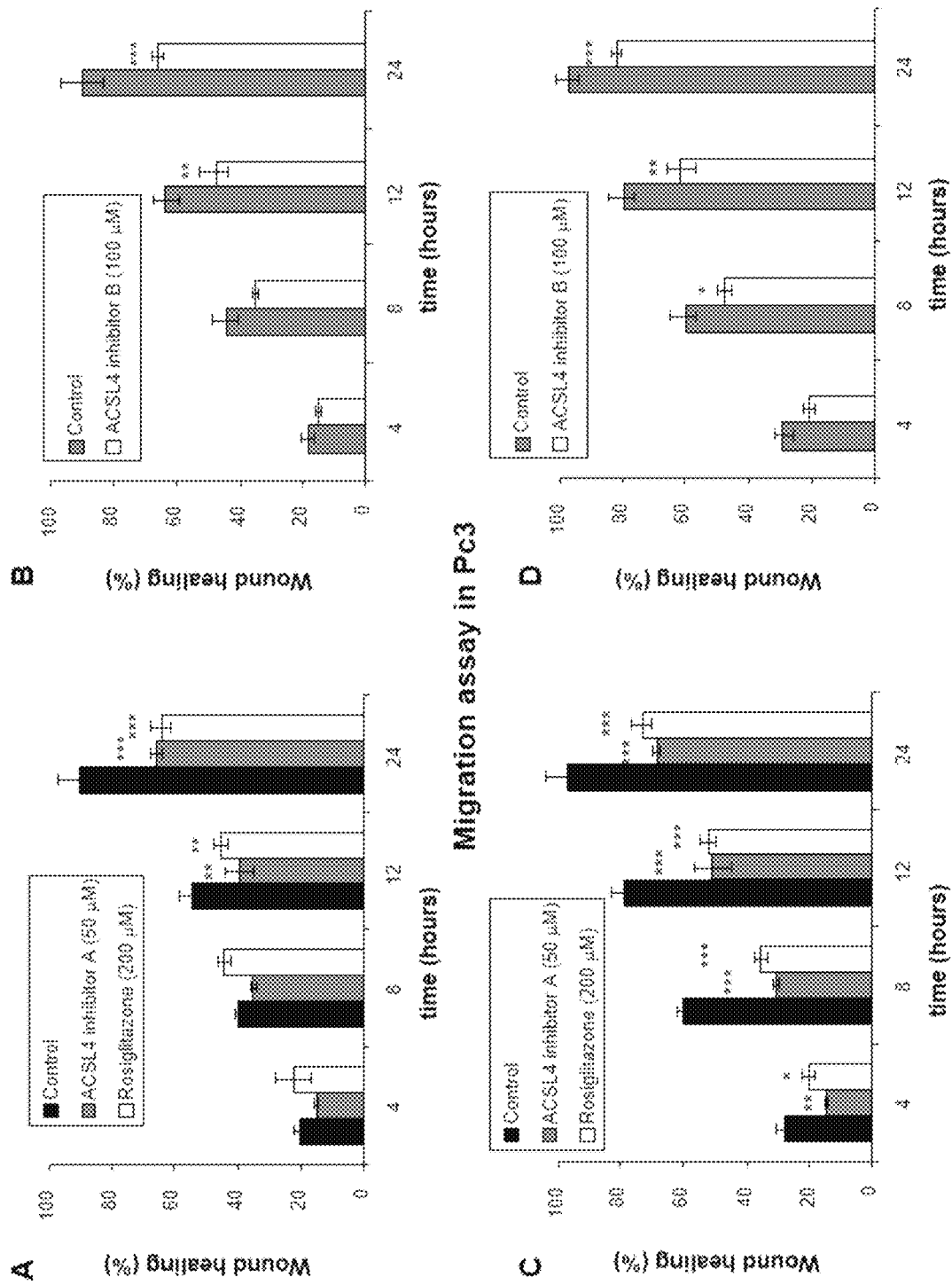
FIG. 4 shows the results obtained in a cell migration assay in MDA MB 231 and Pc-3 cells. A) and C) show wound healing % over time in MDA MB 231 and Pc-3 cells respectively (2000 cells/well) incubated with vehicle (control), compound A (50 μM) and Rosiglitazone (reference compound, 20004) for 12 h. B) and D) show wound healing % over time in MDA MB 231 and Pc-3 respectively cells (2000 cells/well) incubated with vehicle (control) and compound B (100 μM) for 12 h. Bars indicate wound healing % vs time (hours). Data is presented as mean±SD.

ACSL4 inhibitor A succeeded in inhibiting the migration of MDA-MB-231 cells. The inhibitor A of the invention induced a less rapid cell migration toward the injury area in this wound healing assay. Differences in the wound area between cells with and without ACSL4 inhibitor were evident as early as 12 h after injury and at lower concentrations (50 µM) than those required with inhibitor B (100 µM; FIGS. 4B and 4D) or rosiglitazone (200 µM: FIGS. 4A and 4C).

Example 5

ACSL4 Inhibition in Steroidogenesis—Progesterone Production in MA-10 Leydig and Y1 Adrenal Cells In the present example, ACSL4 inhibitor effects on steroid production were tested by stimulating MA 10 Leydig and Y1 adrenal cells with cAMP (0.5 mM) for 1 hour and assessing progesterone levels. MA-10 mouse Leydig tumor cells were generously provided by Dr. Mario Ascoli (University of Iowa, Iowa City, Iowa) and cultured in Waymouth MB/752 medium supplemented with 15% horse serum and antibiotics at 37° C. and 5% $CO_2$ as previously described [4]. The culture medium was replaced with serum-free Waymouth medium before experiments.

Murine Y1 adrenocortical tumor cells were generously provided by Dr B Schimmer (University of Toronto, Toronto, Canada). Methods for the culture of Y1 mouse adrenal tumor cells (American Type Culture Collection, Rockville, MD, USA) have been published elsewhere (Schimmer 1979). Cells were maintained at 37 C in growth medium (HAM F10) containing fetal bovine (2·5%) and horse (12·5%) sera.

Figure 5:
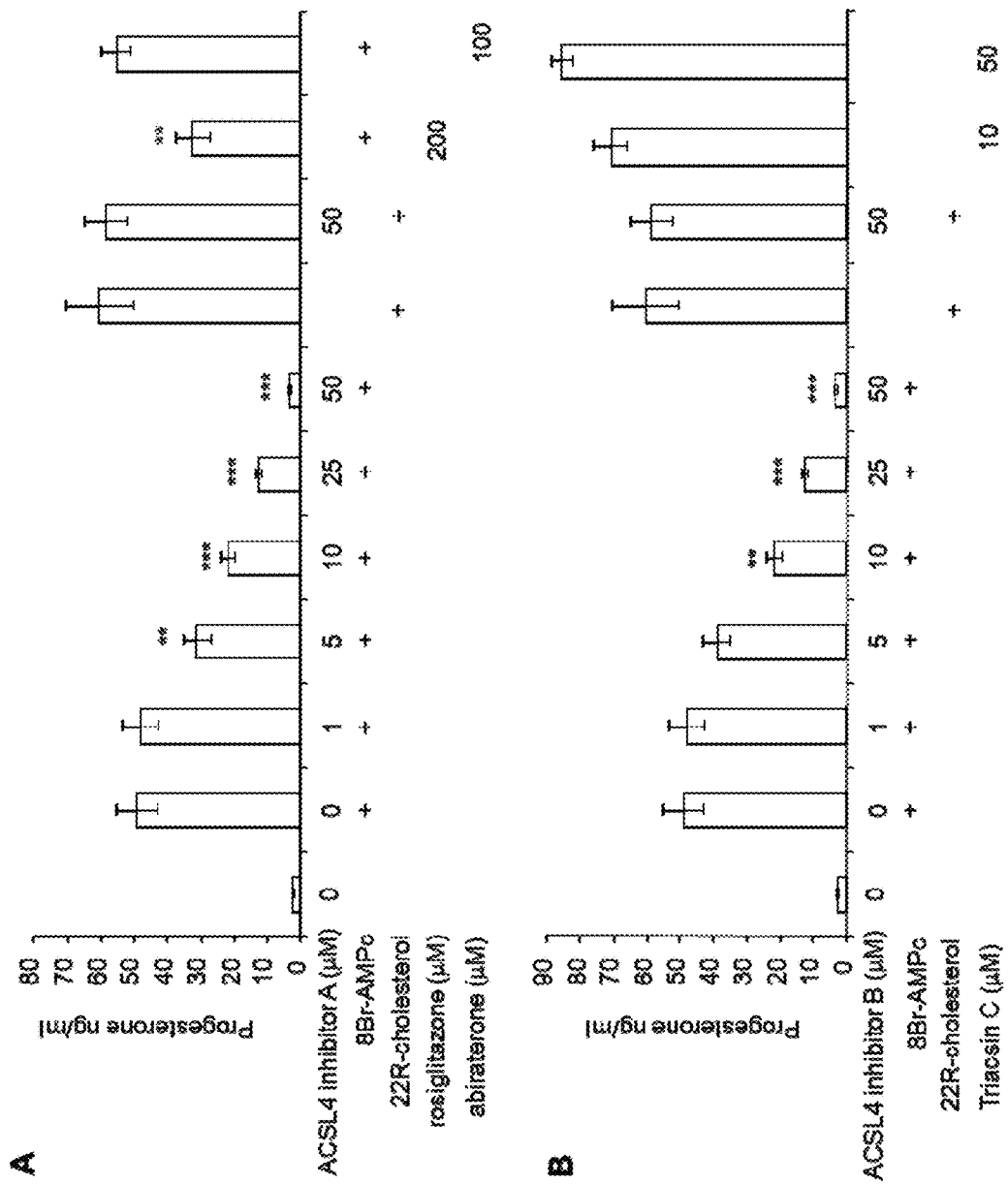
FIG. 5 shows the results obtained by performing a steroidogenesis assay: the effects of ACSL4 inhibition on steroid production (ng/ml) were measured by stimulating MA-10 Leydig cells with cAMP and assessing progesterone levels a very well indicator of Leydig cell function and a precursor of steroids. A) Leydig cells were treated with varying concentrations of compound A (inhibitor A), 8Br-AMPc (used to stimulate steroid production), 22-R-cholesterol (a permeable cholesterol analog which does not require ACSL4 activation), rosiglitazone (for comparative purposes) and abiraterone (a well-known inhibitor of Leydig and adrenal steroidogenesis, used as a reference compound).

The results obtained in this experiment may be seen in FIGS. 5 and 6.

Many ACSL4 inhibitors are described in the prior art, among which Triacsin C and rosiglitazone may be mentioned [15]. In this experiment, ACSL4 inhibitor A succeeded in significantly inhibiting steroid synthesis in the tested cell lines at a minimal concentration of 5 uM, which was lower than the concentration required for inhibitor B (see FIGS. 5B and 6B) or rosiglitazone (see FIGS. 5A and 6A). According to this experiment, the concentrations of inhibitor A which succeeded in inhibiting ACSL4 activity were much lower than those required for rosiglitazone. However, Triacsin C used as reference compound failed to inhibit progesterone synthesis.

As may be seen in FIG. 5, Triacsin C cannot be used as steroid synthesis inhibitor given that at a concentration of from 10 µM already produces a disturbance of the mitochondria membrane and increases the release of steroids in a non-specific manner (a release of progesterone of 3.26 vs 46.5 ng/ml, control vs 10 µM Triacsin C).

Another reference compound used in this case was abiraterone, a well-known inhibitor of Leydig and adrenal steroidogenesis. Abiraterone inhibits steroidogenesis through the inhibition of CYP17, a cytochrome P450 (CYP) enzyme located in the endoplasmic reticulum of the testis, ovaries, adrenals, and placenta. CYP17 drives the synthesis of glucocorticoids and sex hormones, has both 17a hydroxylase and C17,20 lyase activity, and plays a critical role in the production of cortisol and androgen synthesis by inhibiting the conversion of pregnenolone to 17OH pregnenolone and progesterone to 17OH progesterone. Accordingly, abiraterone failed to inhibit progesterone production in Leydig and adrenal cells.

It is worth pointing out that ACSL4 inhibition through compounds A or B of the present invention inhibits cholesterol transport from the outer to the inner mitochondrial membrane, the rate-limiting step in steroid synthesis, and prevents steroid accumulation. This constitutes an advantage over the use of abiraterone, which inhibits androgen and glucocorticoid synthesis but is unable to inhibit progesterone synthesis.

Cell behavior was also assessed in steroidogenesis by using a permeable cholesterol analog which does not require ACSL4 activation (cholesterol 22R). According to the results obtained, which are shown in FIG. 4A, ACSL4 inhibitor exerted no effects on cholesterol 22R action, which proves the specificity of the system as well as the integrity of the mitochondrial process. These findings indicate that steroidogenesis is inhibited as a consequence of ACSL4 inhibition and not due to cell toxicity.

Example 6

3H-Arachidonic Acid Incorporation into MDA-MB-231 Cells

The effects of the ACSL4 inhibitor of the invention were evaluated in MDA-MB-231 cells, in which ACSL4 activity plays a key role in tumor biology.

ACSL4 activity was determined by measuring the transformation of arachidonic acid (AA) into enzyme product arachidonoyl-CoA (AA CoA), through $^3$H-AA incorporation expressed as $CPM/10^6$ cells×$10^{-3}$ with results showing significant ACSL4 inhibition and a consequent significant reduction in AA CoA levels.

ACSL4 activity was stimulated with serum in tumoral cells. Once again, inhibitor A concentrations for inhibiting ACSL4 activity were lower than those required for rosiglitazone. The results obtained for this experiment are shown in FIG. 7A.

The same test was carried out for ACSL4 inhibitor B and results are shown in FIG. 7B.

Example 7

3H-Arachidonic Acid Incorporation into MA-10 Leydig Cells

The effects of the ACSL4 inhibitor of the invention were evaluated in MA-10 Leydig cells, in which ACSL4 activity plays a key role in steroids synthesis.

ACSL4 activity was determined by measuring the transformation of arachidonic acid (AA) into enzyme product arachidonoyl-CoA (AA CoA), through $^3$H-AA incorporation expressed as $CPM/10^6$ cells×$10^{-3}$ with results showing significant ACSL4 inhibition and a consequent significant reduction in AA CoA levels.

ACSL4 activity was stimulated with cAMP. Inhibitor A concentrations for inhibiting ACSL4 activity were lower than those required for rosiglitazone. The results obtained for this experiment are shown in FIG. 8A.

The same test was carried out for ACSL4 inhibitor B and results are shown in FIG. 8B.

Example 8

Analysis of ACSL4 Activity in a Cell Free Assay

Acyl-CoA synthetase activity was measured via a modified protocol by Kim et al. [15], involving the formation of AA-CoA from AA.

Recombinant protein was incubated in the presence of increasing concentrations of inhibitor A (10, 25, 50 and 100 µM), inhibitor B at 100 µM and the reference compound rosiglitazone at 100 µM, for 10 min at 37° C. in a reaction mixture containing 10 mmol/l ATP, and 250 µmol/l CoA with 50 µmol/l AA trace-labeled with [3H]-AA (0.25 µCi) in a final volume of 100 µl.

The reaction was initiated by the addition of the recombinant protein and terminated by the addition of 1 ml of ethyl acetate.

The radioactivity measured was used to calculate the total enzymatic activity. The results are shown in FIG. 9.

Example 9

Cell Proliferation Inhibition in MDA-MB-231 Line by a Compound of the Invention in Combination with an Estrogen Receptor (ER) Inhibitor The effect of a combination of a compound of the invention and 4OH-tamoxifen (ER inhibitor) on cell proliferation was assessed in MDA MB-231 cells. Results are shown in FIG. 10.

MDA-MB-231 cells were plated at a density of 4000 cells/well in 96-well plates with 10% FBS-supplemented D-MEM medium and allowed to adhere overnight at 37° C. in a humidified, 5% $CO_2$ atmosphere. The medium was then changed to serum-free medium. After 24 h, the cells were switched to 10% FBS-supplemented D-MEM medium and incubated with inhibitor A (10 µM) and/or 4-hydroxytamoxifen (4OH-Tam 7.5 µM) for 72 hours. Subsequently, cell proliferation was measured by the bromo-deoxyuridine (BrdU) incorporation assay.

Thus, the combination of inhibitor A and the tamoxifen derivative was much more efficient in inhibiting tumor proliferation than each of the compounds individually. Therefore, this experiment demonstrates the synergism observed when a combination of inhibitor A and OH-tamoxifen is applied (see FIG. 10A).

The same assay was performed with inhibitor B at a concentration of 20 µM combined with 4OH-Tam 7.5 µM. Results are shown in FIG. 10B. Inhibitor B also increases proliferation inhibition of the tumor cell line assessed. Additionally, the combination of inhibitor B and OH-tamoxifen also shows a synergistical behavior.

Example 10

Cell Proliferation Inhibition in MDA-MB-231 Line by Inhibitor of the Invention in Combination with Chemotherapeutic Agents The effect of different combinations of inhibitor A of the invention and three reference chemotherapeutic agents on cell proliferation was assessed in MDA MB-231 cells.

MDA-MB-231 cells were plated at a density of 4000 cells/well in 96-well plates with 10% FBS-supplemented D-MEM medium and allowed to adhere overnight at 37° C. in a humidified, 5% CO2 atmosphere. The medium was then changed to serum-free medium. After 24 h, the cells were switched to 10% FBS-supplemented D-MEM medium and then incubated with inhibitor A (10 µM) and/or cisplatin (1 µM), doxorubicin (0.25 µM) and paclitaxel (0.1 µM) for 72 hours. Subsequently, cell proliferation was measured through BrdU incorporation assays.

Thus, the combination of inhibitor A and the chemotherapeutic agents was much more efficient in inhibiting tumor proliferation than each of the compounds individually. Therefore, this experiment demonstrates the synergism observed when a combination of inhibitor A and OH-Tamoxifen is applied (see FIG. 11).

Example 11

Study of Tumor Growth Using the Chick Embryo Chorioallantoic Membrane (CAMP) Assay.

In this experiment, the in vivo CAM assay platform of IPATIMUP was used to test the effect of inhibitor A to inhibit tumor growth in vivo. The CAMP is a preclinical in vivo model for drug screening.

Chicken eggs in the early phase of breeding are between in vitro and in vivo systems and provide a vascular test environment not only to study angiogenesis but also to study tumorigenesis. Since the lymphoid system is not fully developed until late stages of incubation, the chick embryo serves as a naturally immunodeficient host capable of sustaining grafted tissues and cells without species-specific restrictions.

As previously described, breast cancer MDA-MB231 cell line was used as a cell model to assess tumor cell growth. The effects of the compound were compared to those of the vehicle (DMEM).

The test compound, at the 10 µM and 100 µM, were inoculated together with $0.5 \times 10^6$ MDA-MB231 cells into a total of 53 eggs (distributed in two independent experiments), at embryonic development day (EDD) 10. The effects of the compound A were compared to those of the vehicle (DMEM).

Xenografted cells/tumors were treated in ovo on EDD12 and the experiment ended at EDD 14. At the endpoint, CAMs were fixed (with paraformaldehyde), excised from the embryo and photographed ex ovo. Results are shown in FIG. 12.

The pictures were used to determine the number of neo vessels growing radially towards the inoculation site. Pictures were used to determine the tumor area using the same software (Cell sens from Olympus).

Statistical analysis of data was performed by applying the Kruskal-Wallis test which is a nonparametric test that compares three or more unmatched groups and it was used to compare the experimental groups. Significant statistical differences were found between Vehicle and Compound A (100 µM). A post hoc analysis (Dunns' multiple comparison test) was performed to determine the p value of each of the test conditions in comparison to the control condition (vehicle), n=36 for inhibitor 1 and n=17 for vehicle, p value (Kruskal-Wallis)<0.0001.

Example 12

Study of Steroidogenesis in Male Mice and in Prostate Cancer Cells.

Thirty-day-old male BALB/c mice were treated with inhibitor A (10-100 µM) i.p at a dose of 50 ul/mice. After 3 hours the animal received a single s.c injection of human Chorionic Gonadotrophin (300 U/mice). After 3 hours the animal were sacrificed and assessed for testosterone, pregnenolone and progesterone levels FIG. 13 A, corticosterone FIG. 13 B and steroids in Pc-3 cell FIG. 13 C.

The effects of ACSL4 inhibition on steroid production in Pc-3 cells were measured by stimulating the cells with serum free of steroids for 24 hs. Steroids synthesis was measured in the medium after extraction with the Strata C18-T (55 µm, 140 A) from phenomenex (Torrance CA, USA).

ACSL4 inhibitor A succeeded in significantly inhibiting steroid synthesis at a minimal concentration of 25 uM. According to this experiment, the inhibitor A succeeded in inhibiting ACSL4 activity in an in vivo model.

It is to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

REFERENCES

[1] M. J. Kang, T. Fujino, H. Sasano, H. Minekura, N. Yabuki, H. Nagura, H. Iijima, T. T. Yamamoto, A novel arachidonate-preferring acyl-CoA synthetase is present in steroidogenic cells of the rat adrenal, ovary, and testis, Proc Natl Acad Sci USA 94(7) (1997) 2880-4.

[2] A. Gazou, A. Riess, U. Grasshoff, K. Schaferhoff, M. Bonin, A. Jauch, O. Riess, A. Tzschach, Xq22.3-q23 deletion including ACSL4 in a patient with intellectual disability, Am J Med Genet A 161A(4) (2013) 860-4.

[3] H. R. Modi, M. Basselin, A. Y. Taha, L. O. Li, R. A. Coleman, M. Bialer, S. I. Rapoport, Propylisopropylacetic acid (PIA), a constitutional isomer of valproic acid, uncompetitively inhibits arachidonic acid acylation by rat acyl-CoA synthetase 4: a potential drug for bipolar disorder, Biochim Biophys Acta 1831(4) (2013) 880-6.

[4] P. Maloberti, R. Castilla, F. Castillo, F. Cornejo Maciel, C. F. Mendez, C. Paz, E. J. Podesta, Silencing the expression of mitochondrial acyl-CoA thioesterase I and acyl-CoA synthetase 4 inhibits hormone-induced steroidogenesis, The FEBS journal 272(7) (2005) 1804-14.

[5] Y. Cao, K. B. Dave, T. P. Doan, S. M. Prescott, Fatty acid CoA ligase 4 is up-regulated in colon adenocarcinoma, Cancer research 61(23) (2001) 8429-34.

[6] U. D. Orlando, A. F. Castillo, M. A. Dattilo, A. R. Solano, P. M. Maloberti, E. J. Podesta, Acyl-CoA synthetase-4, a new regulator of mTOR and a potential therapeutic target for enhanced estrogen receptor function in receptor-positive and -negative breast cancer, Oncotarget 6(40) (2015) 42632-50.

[7] U. D. Orlando, J. Garona, G. V. Ripoll, P. M. Maloberti, A. R. Solano, A. Avagnina, D. E. Gomez, D. F. Alonso, E. J. Podesta, The functional interaction between Acyl-CoA synthetase 4, 5-lipooxygenase and cyclooxygenase-2 controls tumor growth: a novel therapeutic target, PloS one 7(7) (2012) e40794.

[8] M. E. Monaco, C. J. Creighton, P. Lee, X. Zou, M. K. Topham, D. M. Stafforini, Expression of Long-chain Fatty Acyl-CoA Synthetase 4 in Breast and Prostate Cancers Is Associated with Sex Steroid Hormone Receptor Negativity, Transl Oncol 3(2) (2010) 91-8.

[9] X. Wu, Y. Li, J. Wang, X. Wen, M. T. Marcus, G. Daniels, D. Y. Zhang, F. Ye, L. H. Wang, X. Du, S. Adams, B. Singh, J. Zavadil, P. Lee, M. E. Monaco, Long chain fatty Acyl-CoA synthetase 4 is a biomarker for and mediator of hormone resistance in human breast cancer, PloS one 8(10) (2013) e77060.

[10] X. Wu, F. Deng, Y. Li, G. Daniels, X. Du, Q. Ren, J. Wang, L. H. Wang, Y. Yang, V. Zhang, D. Zhang, F. Ye, J. Melamed, M. E. Monaco, P. Lee, ACSL4 promotes prostate cancer growth, invasion and hormonal resistance, Oncotarget 6(42) (2015) 44849-63.

[11] C. Paz, F. Cornejo Maciel, A. Gorostizaga, A. F. Castillo, M. M. Mori Sequeiros Garcia, P. M. Maloberti, U. D. Orlando, P. G. Mele, C. Poderoso, E. J. Podesta, Role of Protein Phosphorylation and Tyrosine Phosphatases in the Adrenal Regulation of Steroid Synthesis and Mitochondrial Function, Frontiers in endocrinology 7 (2016) 60.

[12] C. Poderoso, P. Maloberti, A. Duarte, I. Neuman, C. Paz, F. C. Maciel, E. J. Podesta, Hormonal activation of a kinase cascade localized at the mitochondria is required for StAR protein activity, Mol Cell Endocrinol 300(1-2) (2009) 37-42.

[13] P. Maloberti, R. C. Lozano, P. G. Mele, F. Cano, C. Colonna, C. F. Mendez, C. Paz, E. J. Podesta, Concerted regulation of free arachidonic acid and hormone-induced steroid synthesis by acyl-CoA thioesterases and acyl-CoA synthetases in adrenal cells, European journal of biochemistry 269(22) (2002) 5599-607.

[14] P. Maloberti, R. Castilla, F. Castillo, F. C. Maciel, C. F. Mendez, C. Paz, E. J. Podesta, Silencing the expression of mitochondrial acyl-CoA thioesterase I and acyl-CoA synthetase 4 inhibits hormone-induced steroidogenesis, The FEBS journal 272(7) (2005) 1804-14.

[15] J. H. Kim, T. M. Lewin, R. A. Coleman, Expression and characterization of recombinant rat Acyl-CoA synthetases 1, 4, and 5. Selective inhibition by triacsin C and thiazolidinediones, The Journal of biological chemistry 276(27) (2001) 24667-73.

The invention claimed is:

1. A compound (N-(4-(3-(5-methylfuran-2-yl)-1-phenyl-1H-pyrazol-4-yl)-3,4-dihydrobenzo[4,5]imidazo[1,2-α][1,3,5]triazin-2-yl)acetamide) of formula A,

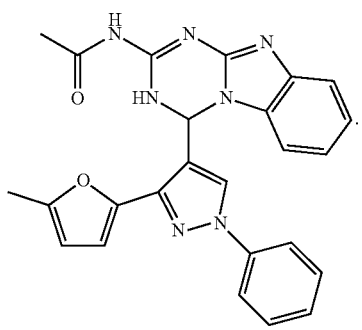

A an enantiomer, solvate, or pharmaceutically acceptable salt thereof.

2. A process for preparing the compound of formula A according to claim 1, comprising reacting 4-(3-(5-methylfuran-2-yl)-1-phenyl-1H-pyrazol-4-yl)-3,4-dihydrobenzo[4,5]imidazo[1,2-a][1,3,5]triazin-2-amine with acetic anhydride.

3. The process according to claim 2, comprising reacting 4-(3-(5-methylfuran-2-yl)-1-phenyl-1H-pyrazol-4-yl)-3,4-dihydrobenzo[4,5]imidazo[1,2-α][1,3,5]triazin-2-amine (formula B) with acetic anhydride, according to the following reaction:

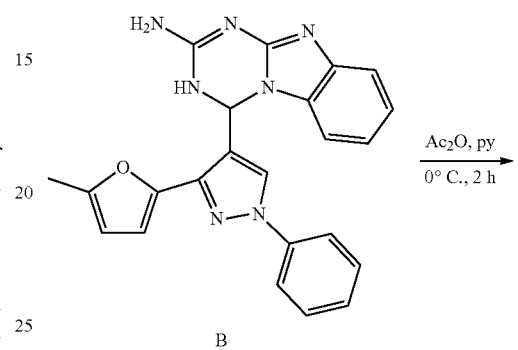

B

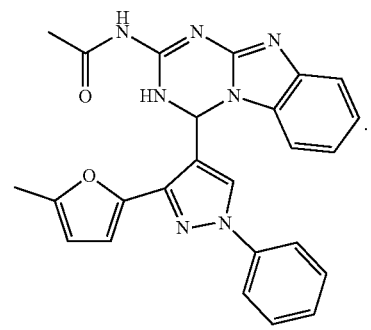

A

4. A method for treating a patient having prostate cancer, breast cancer or triple negative breast cancer (TNBC), comprising administering to the patient a compound of formula A

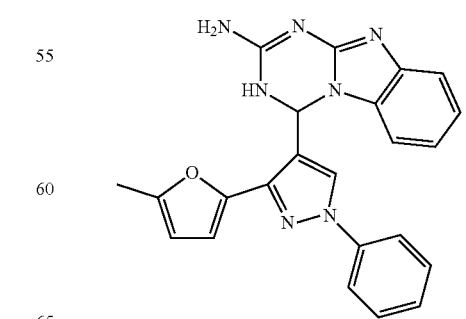

B or a compound of formula B

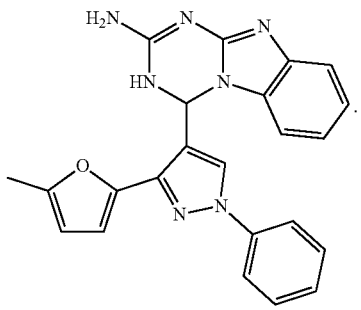

5. The method according to claim 4, comprising administering the compound of formula A or the compound of formula B in combination with a chemotherapeutic agent.

6. The method according to claim 5, wherein the chemotherapeutic agent is selected from doxorubicin, paclitaxel and cisplatin.

7. The method according to claim 4, comprising administering the compound of formula A or the compound of formula B in combination with an estrogen receptor (ER) inhibitor.

8. The method according to claim 7, wherein the ER inhibitor is selected from the group consisting of tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

* * * * *